(12) United States Patent
Burke

(10) Patent No.: US 8,563,018 B2
(45) Date of Patent: Oct. 22, 2013

(54) FOAMABLE PESTICIDE COMPOSITIONS

(75) Inventor: Terrence R. Burke, Kirkwood, MO (US)

(73) Assignee: BASF Corporation, Florham Park, NJ (US)

( * ) Notice: Subject to any disclaimer, the term of this patent is extended or adjusted under 35 U.S.C. 154(b) by 401 days.

(21) Appl. No.: 12/769,403

(22) Filed: Apr. 28, 2010

(65) Prior Publication Data

US 2010/0323897 A1    Dec. 23, 2010

Related U.S. Application Data

(60) Provisional application No. 61/173,283, filed on Apr. 28, 2009, provisional application No. 61/237,977, filed on Aug. 28, 2009.

(51) Int. Cl.
*A01N 25/00* (2006.01)
(52) U.S. Cl.
USPC ............ 424/405; 514/945; 504/139; 504/358
(58) Field of Classification Search
USPC .................... 424/405; 514/945; 504/139, 358
See application file for complete search history.

(56) References Cited

U.S. PATENT DOCUMENTS

| | | | |
|---|---|---|---|
| 4,889,710 A | 12/1989 | Hagarty | |
| 5,527,760 A | 6/1996 | Rensing et al. | |
| 5,814,325 A | 9/1998 | Rod | |
| 6,139,858 A | 10/2000 | Fujimoto | |
| 6,415,956 B1 | 7/2002 | Havlovitz | |
| 6,840,461 B1 | 1/2005 | Burke et al. | |
| 8,153,560 B2 | 4/2012 | Langewald et al. | |
| 2001/0036935 A1 | 11/2001 | Renello et al. | |
| 2003/0108585 A1 | 6/2003 | Roe et al. | |
| 2003/0152605 A1 | 8/2003 | Martin et al. | |
| 2003/0220296 A1 | 11/2003 | Besser et al. | |
| 2004/0057977 A1* | 3/2004 | Gardner et al. | 424/410 |
| 2004/0253287 A1 | 12/2004 | Denton | |
| 2007/0020304 A1* | 1/2007 | Tamarkin et al. | 424/405 |
| 2007/0049496 A1* | 3/2007 | Messerschmidt et al. | 504/357 |
| 2008/0118585 A1 | 5/2008 | Nouvel | |
| 2011/0160054 A1 | 6/2011 | Breuningger et al. | |
| 2011/0224075 A1 | 9/2011 | Kordes et al. | |

FOREIGN PATENT DOCUMENTS

| | | | |
|---|---|---|---|
| CN | 101081024 A | 12/2007 | |
| EP | 0400914 A1 | 5/1990 | |
| EP | 0400914 A1 | 12/1990 | |
| WO | 02052940 A1 | 7/2002 | |
| WO | 2007104720 A1 | 9/2007 | |
| WO | 2009036797 A1 | 3/2009 | |

OTHER PUBLICATIONS

International Search Report and Written Opinion for International Application No. PCT/US2010/032795 mailed Jul. 21, 2010, 18 pages.
Material Safety Data Sheet for PREMISE Foam, Bayer Environmental Science, Jun. 12, 2006, 7 pages.
Product Label for PREMISE Foam, Bayer Environmental Science, May 13, 2004, 4 pages.
Material Safety Data Sheet for FASTOUT CS Foam, Whitmire Micro-Gen Research Laboratories, Inc., Nov. 21, 2006, 2 pages.
Product Label for Label for FASTOUT CS Foam, Whitmire Micro-Gen Research Laboratories, Inc., 2007, 2 pages.
Material Safety Data Sheet ALPINE Ant and Termite Foam, Whitmire Micro-Gen Research Laboratories, Inc., Apr. 6, 2006, 2 pages.
Product Label for ALPINE Ant and Termite Foam, Whitmire Micro-Gen Research Laboratories, Inc., 2009, 2 pages.
Kwaambwa, "Stability and phase separation behaviour of systems of particles in a medium with added polymer", retrieved from internet: http://www.wrc.org.za.
Konk Insecticide Foam, retrieved from internet: www.pestsupplystore.com/Pesticides/Labels/Konk-Foam-Label.pdf.
CN Office Action from corresponding CN Application No. 201080028973.6, Jan. 23, 2013.
Office Action for U.S. Appl. No. 13/607,249 dated Jan. 28, 2013; 25 pages.
Pesticide Residues in Food—1997, retrieved from internet: http://www.inchem.org/documents/jmpr/jmpmono/v097pr09.htm.
Kwaambwa, "Stability and phase separation behaviour of systems of particles in a medium with added polymer", retrieved from internet: http://www.wrc.org.za, Jan. 1, 2006.
Konk Insecticide Foam, retrieved from internet: www.pestsupplystore.com/Pesticides/Labels/Konk-Foam-Label.pdf, Feb. 2004.
BASF, Termidor SC Terminticide/Insecticide, 2005, Label, 12 pages.
Bayer Environmental Science, Suspend SC, 205, Label, 9 pages, Apr. 5, 2005.
Profoam Platinum, Nothing Else Stacks Up, 2008, Label, 3 pages.
Vanderbilt, Xanthan Gum, 2000, Label, 16 pages.
Kobayashi N., et al., Foamable Aerosol Agent for Exterminating Harmful Insects Such as Ant, Cockroach, Wood Louse and Stink Bug, XP002590413, 2 pages, Feb. 14, 2002.
International Search Report and Written Opinion for PCT/US2010/032789, dated Jul. 14, 2011; 18 pages.

* cited by examiner

*Primary Examiner* — Rebecca Prouty
*Assistant Examiner* — Danielle Sullivan
(74) *Attorney, Agent, or Firm* — Armstrong Teasdale LLP

(57) ABSTRACT

Ready-to-use foamable pesticide compositions that contain a particulate pesticide suspended therein and applicators for dispensing such compositions. Methods for treating pests such as arthropods by contacting pests with such compositions are also provided.

11 Claims, 3 Drawing Sheets

FOAMABLE PESTICIDE COMPOSITIONS

CROSS-REFERENCE TO RELATED APPLICATIONS

This application claims the benefit of U.S. Provisional Application No. 61/173,283, filed Apr. 28, 2009, and of U.S. Provisional No. 61/237,977, filed Aug. 28, 2009, both of which are incorporated herein in their entirety.

BACKGROUND

The field of the disclosure relates to pesticide compositions and, more particularly, ready-to-use foamable pesticide compositions that contain a particulate pesticide. The field of the disclosure also relates to pesticide applicators and methods for controlling pests. The pesticide compositions of embodiments of the present disclosure are well-suited for general application but are particularly well-suited for treating arthropods including insects and, particularly, for treating termites, ants, cockroaches and beetles.

Insects and other arthropod pests can have negative effects on the quality of human life. For instance, when found in the home, insects and other arthropods can be a source of annoyance due purely to their presence. They may also spread disease and allergens. Additionally, when found on plants and crops, insects and other pest arthropods can destroy foliage and fruit, and may adversely affect plant and crop growth, quality, and yield.

Among the insects which are particularly undesirable are termites. Termites are well known for their destructive effects on residences, businesses and various other structures. The damage from termite infestations results in huge economic losses, structural safety concerns, and destruction of architecturally valuable structures. Ants are also particularly undesirable. Some species of ants are known to damage crops and others may bite humans or pets as an attack or defense mechanism. Cockroaches and beetles are also undesirable pests. Cockroaches may carry a number of organisms that cause disease and beetles are known to damage food and residential and commercial structures.

It is domestically and commercially desirable to control termites and ants through the use of pesticide products. It is also desirable to control other crawling arthropods, such as cockroaches, beetles, earwigs, silverfish, crickets, spiders, centipedes, millipedes, scorpions, pillbugs, sowbugs and various flying insects including flies, mosquitoes, gnats, moths, wasps, hornets, bees and the like.

A broad range of compounds have been found to be toxic to insects and other arthropods such that formulations containing the compounds may be used for their control. However, many arthropods inhabit spaces and voids both inside and outside residential and commercial structures in which it is difficult to apply the compounds. For instance, pests may inhabit voids within walls that contain plumbing and electrical structures that limit application of a pesticide. There is a continuing need for new compositions, products and methods that enable toxic compounds to be applied to hard-to-reach locations which host pests.

In many instances, proper treatment includes application of such compositions to the entire exterior perimeter of structures to act as a barrier for entry of pests or to ensure that pests entering and exiting the structure contact the pesticide. In such exterior applications, a homeowner or pest control professional applies the composition to an exterior surface of the structure, such as near the base thereof, and/or on the ground surface near the structure and/or on other exterior surfaces such as landscape timber or open area ground surfaces. Compositions used for conventional exterior applications are typically applied in liquid form, which renders it difficult for the person applying the treatment to readily determine which areas have been treated and which have not. This can result in under- or over-application of the composition.

There is a also a continuing need for compositions, application devices and associated application methods that enable toxic compounds to be applied over broad surfaces such as around the exterior perimeter of a building structure, landscape materials, ground surfaces, and the like. There is also a need for such compositions, application devices and application methods that enable persons applying the compositions to track where the composition has been applied during a treatment process.

SUMMARY

In one aspect of the present disclosure, a ready-to-use foamable pesticide composition comprises a diluent, a particulate pesticide suspended in the diluent, a thickening agent and a surfactant system comprising at least one surfactant.

In another aspect of the present disclosure, a pesticide applicator for applying pesticide to pests includes a container and a pesticide composition within the container. The pesticide composition includes a diluent, a particulate pesticide suspended in the diluent, a thickening agent and a surfactant system comprising at least one surfactant.

Various refinements exist of the features noted in relation to the above-mentioned aspects of the present invention. Further features may also be incorporated in the above-mentioned aspects of the present invention as well. These refinements and additional features may exist individually or in any combination. For instance, various features discussed below in relation to any of the illustrated embodiments of the present invention may be incorporated into any of the above-described aspects of the present invention, alone or in any combination.

BRIEF DESCRIPTION OF THE DRAWINGS

Corresponding reference characters indicate corresponding parts throughout the drawings.

DETAILED DESCRIPTION

Figure 1:
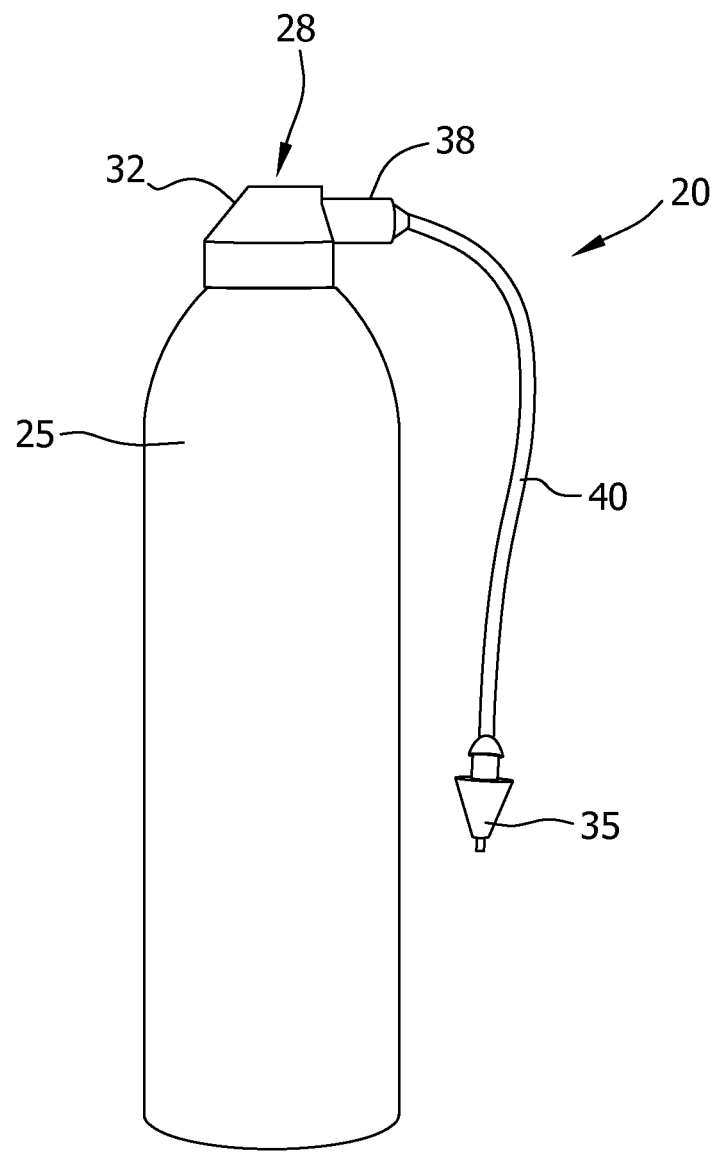
FIG. 1 is a front-side view of a pesticide applicator according to one embodiment of the present disclosure.

Among the provisions of the present disclosure are ready-to-use foamable pesticide compositions, pesticide applicators and methods for controlling pests. It has been found that in embodiments of the present disclosure, a toxic chemical (e.g., fipronil) may generally be included in a composition that includes a diluent, thickening agent and a surfactant system. In certain embodiments, the pesticide is in a particulate form and the particulate is suspended in the composition. The composition of certain embodiments is generally foamable upon application allowing the composition to be applied in hard-to-reach voids, spaces and crevices. Once applied, the composition expands to fill the void, space or crevice allowing for greater bioavailability of the pesticide and for more effective control of the target pest. For instance, the pesticide composition of embodiments of the present disclosure may be applied to an insect gallery or tunnel or to a constricted area within a structure. Upon application, the composition generally foams and flows within the void and around obstructions to provide more complete coverage of the target site of application leading to better control of insects and other arthropods.

It has also been found that the foaming-action of the pesticide composition allows those applying the composition to track where the pesticide composition has been applied which prevents over- and under-application of the composition. This is particularly beneficial when applying the composition in outdoor areas, such as about the perimeter of a building structure. The foaming composition, according to certain embodiments, is generally fast-breaking which allows the composition to visually disappear shortly after application such that it is unlikely that the formulation is visibly observed by persons other than the person applying the composition such as, for example, a homeowner.

Ready-to-Use Foamable Pesticide Composition

In one embodiment of the present disclosure, a ready-to-use foamable pesticide composition is provided. For purposes of the present disclosure, "ready-to-use" refers to compositions that are not in a concentrate form but rather which may be applied without modification of the relative amounts of components within the product. In this regard, as used herein, the term "pesticide" refers to any substance or mixture for preventing, destroying, repelling, or mitigating any pest including insects, animals (e.g., mice, rats), plants (e.g., weeds), fungi, microorganisms (e.g., bacteria and viruses), pseudocoelomates (e.g., nematodes) and prions. The term "arthropodicide", which is a type of pesticide, is used herein to mean any substance or mixture for preventing, destroying, repelling, or mitigating arthropods. The term "insecticide", which is a type of pesticide, is used herein to mean any substance or mixture for preventing, destroying, repelling, or mitigating insects. The term "termiticide", which is a type of insecticide, is used herein to mean any substance or mixture for preventing, destroying, repelling, or mitigating termites.

Suitable pesticides which may be included in the compositions of the present disclosure (and particularly, suitable arthropodicides and/or insecticides) include the following list of compounds ("M compounds"):

(M1) Organo(thio)phosphate compounds: acephate, azamethiphos, azinphos-ethyl, azinphos-methyl, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;

(M2) carbamate compounds: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate;

(M3) pyrethroid compounds: acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin and transfluthrin;

(M4) juvenile hormone mimics: hydroprene, kinoprene, methoprene, fenoxycarb and pyriproxyfen;

(M5) nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), spinetoram (allosteric agonist), thiacloprid, thiocyclam, thiosultap-sodium and AKD1022;

(M6) GABA gated chloride channel antagonist compounds: chlordane, endosulfan, gamma-HCH (lindane); ethiprole, fipronil, pyrafluprole and pyriprole (M7) chloride channel activators: abamectin, emamectin benzoate, milbemectin and lepimectin;

(M8) METI I compounds: fenazaquin, fenpyroximate, pyrimidifen, pyridaben, tebufenpyrad, tolfenpyrad, flufenerim, rotenone;

(M9) METI II and III compounds: acequinocyl, fluacyprim and hydramethylnon;

(M10) uncouplers of oxidative phosphorylation: chlorfenapyr and DNOC;

(M11) inhibitors of oxidative phosphorylation: azocyclotin, cyhexatin, diafenthiuron, fenbutatin oxide, propargite and tetradifon;

(M12) moulting disruptors: cyromazine, chromafenozide, halofenozide, methoxyfenozide and tebufenozide;

(M13) synergists: piperonyl butoxide and tribufos;

(M14) sodium channel blocker compounds: indoxacarb and metaflumizone;

(M15) selective feeding blockers: crylotie, pymetrozine and flonicamid;

(M16) mite growth inhibitors: clofentezine, hexythiazox and etoxazole;

(M17) chitin synthesis inhibitors: buprofezin, bistrifluoron, chlorfluazuron, diflubenzuron, flucycloxuron, flufenoxuron, hexaflumuron, lufenuron, novaluron, noviflumuron, teflubenzuron and triflumuron;

(M18) lipid biosynthesis inhibitors: spirodiclofen, spiromesifen and spirotetramat;

(M19) octapaminergic agonsits: amitraz;

(M20) ryanodine receptor modulators: flubendiamide and the phtalamid compound (R) —, (S)-3-Chlor-N-1-{2-methyl-4-[1,2,2,2-tetrafluor-1-(trifluormethyl)ethyl]phenyl}-N2-(1-methyl-2-methylsulfonylethyl)phthalamid (M20.1);

(M21) isoxazoline compounds: 4-[5-(3,5-Dichloro-phenyl)-5-trifluoromethyl-4,5-dihydro-isoxazol-3-yl]-2-methyl-N-pyridin-2-ylmethyl-benzamide (M21.1), 4-[5-(3,5-Dichloro-phenyl)-5-trifluoromethyl-4,5-dihydro-isoxazol-3-yl]-2-methyl-N-(2,2,2-trifluoro-ethyl)-benzamide (M21.2), 4-[5-(3,5-Dichloro-phenyl)-5-trifluoromethyl-4,5-dihydro-isoxazol-3-yl]-2-methyl-N-[(2,2,2-trifluoro-ethylcarbamoyl)-methyl]-benzamide (M21.3), 4-[5-(3,5-Dichloro-phenyl)-5-trifluoromethyl-4,5-dihydro-isoxazol-3-yl]- naphthalene-1-carboxylic acid [(2,2,2-trifluoro-ethylcarbamoyl)-methyl]-amide (M21.4), 4-[5-(3,5-Dichlorophenyl)-5-trifluoromethyl-4,5-dihydro-isoxazol-3-yl]-N-[(methoxyimino)methyl]-2-methylbenzamide (M21.5) 4-[5-(3-Chloro-5-trifluoromethyl-phenyl)-5-trifluoromethyl-4,5-dihydro-isoxazol-3-yl]-2-methyl-N-[(2,2,2-trifluoro-ethylcarbamoyl)-methyl]-benzamide (M21.6), 4-[5-(3-Chloro-5-trifluoromethyl-phenyl)-5-trifluoromethyl-4, 5-dihydro-isoxazol-3-yl]-naphthalene-1-carboxylic acid [(2,2,2-trifluoro-ethylcarbamoyl)-methyl]-amide (M21.7) and 5-[5-(3,5-Dichloro-4-fluoro-phenyl)-5-trifluoromethyl-4,5-dihydro-isoxazol-3-yl]-2-[1,2,4]triazol-1-yl-benzonitrile (M21.8);

(M22) anthranilamide compounds: chlorantraniliprole, cyantraniliprole, 5-Bromo-2-(3-chloro-pyridin-2-yl)-2H-pyrazole-3-carboxylic acid [4-cyano-2-(1-cyclopropyl-ethylcarbamoyl)-6-methyl-phenyl]-amide (M22.1), 5-Bromo-2-(3-chloro-pyridin-2-yl)-2H-pyrazole-3-carboxylic acid [2-chloro-4-cyano-6-(1-cyclopropyl-ethylcarbamoyl)-phenyl]-amide (M22.2), 5-Bromo-2-(3-chloro-pyridin-2-yl)-2H-pyrazole-3-carboxylic acid [2-bromo-4-cyano-6-(1-cyclopropyl-ethylcarbamoyl)-phenyl]-amide (M22.3), 5-Bromo-2-(3-chloro-pyridin-2-yl)-2H-pyrazole-3-carboxylic acid [2-bromo-4-chloro-6-(1-cyclopropyl-ethylcarbamoyl)-phenyl]-amide (M22.4), 5-Bromo-2-(3-chloro-pyridin-2-yl)-2H-pyrazole-3-carboxylic acid [2,4-dichloro-6-(1-cyclopropyl-ethylcarbamoyl)-phenyl]-amide (M22.5), 5-Bromo-2-(3-chloro-pyridin-2-yl)-2H-pyrazole-3-carboxylic acid [4-chloro-2-(1-cyclopropyl-ethylcarbamoyl)-6-methyl-phenyl]-amide (M22.6), N'-(2-{[5-Bromo-2-(3-chloro-pyridin-2-yl)-2H-pyrazole-3-carbonyl]-amino}-5-chloro-3-methyl-benzoyl)-hydrazinecarboxylic acid methyl ester (M22.7), N'-(2-{[5-Bromo-2-(3-chloro-pyridin-2-yl)-2H-pyrazole-3-carbonyl]-amino}-5-chloro-3-methyl-benzoyl)-N'-methyl-hydrazinecarboxylic acid methyl ester (M22.8), N'-(2-{[5-Bromo-2-(3-chloro-pyridin-2-yl)-2H-pyrazole-3-carbonyl]-amino}-5-chloro-3-methyl-benzoyl)-N,N'-dimethyl-hydrazinecarboxylic acid methyl ester (M22.9), N'-(3,5-Dibromo-2-{[5-bromo-2-(3-chloro-pyridin-2-yl)-2H-pyrazole-3-carbonyl]-amino}-benzoyl)-hydrazinecarboxylic acid methyl ester (M22.10), N'-(3,5-Dibromo-2-{[5-bromo-2-(3-chloro-pyridin-2-yl)-2H-pyrazole-3-carbonyl]-amino}-benzoyl)-N'-methyl-hydrazinecarboxylic acid methyl ester (M22.11) and N'-(3,5-Dibromo-2-{[5-bromo-2-(3-chloro-pyridin-2-yl)-2H-pyrazole-3-carbonyl]-amino}-benzoyl)-N,N'-dimethyl-hydrazinecarboxylic acid methyl ester (M22.12);

(M23) malononitrile compounds: 2-(2,2,3,3,4,4,5,5-octafluoropentyl)-2-(3,3,3-trifluoro-propyl)malononitrile (CF2H—CF2-CF2-CF2-CH2-C(CN)2-CH2-CH2-CF3) (M23.1) and 2-(2,2,3,3,4,4,5,5-octafluoropentyl)-2-(3,3,4,4,4-pentafluorobutyl)-malonodinitrile (CF2H—CF2-CF2-CF2-CH2-C(CN)2-CH2-CH2-CF2-CF3) (M23.2);

(M24) microbial disruptors: *Bacillus thuringiensis* subsp. *Israelensi*, *Bacillus sphaericus*, *Bacillus thuringiensis* subsp. *Aizawai*, *Bacillus thuringiensis* subsp. *Kurstaki* and *Bacillus thuringiensis* subsp. *Tenebrionis*;

(M25) aminofuranone compounds: 4-{[(6-Bromopyrid-3-yl)methyl](2-fluoroethyl)amino}furan-2(5H)-on (M25.1), 4-{[(6-Fluoropyrid-3-yl)methyl](2,2-difluoroethyl)amino}furan-2(5H)-on (M25.2), 4-{[(2-Chloro1,3-thiazolo-5-yl)methyl](2-fluoroethyl) amino}furan-2(5H)-on (M25.3), 4-{[(6-Chloropyrid-3-yl)methyl](2-fluoroethyl)amino}furan-2(5H)-on (M25.4), 4-{[(6-Chloropyrid-3-yl)methyl] (2,2-difluoro ethyl)amino}furan-2(5H)-on (M25.5), 4-{[(6-Chloro-5-fluoropyrid-3-yl)methyl](methyl) amino}furan-2(5H)-on (M25.6), 4-{[(5,6-Dichloropyrid-3-yl)methyl] (2-fluoroethyl) amino}furan-2(5H)-on (M25.7), 4-{[(6-Chloro-5-fluoropyrid-3-yl)methyl](cyclopropyl)amino}furan-2 (5H)-on (M25.8), 4-{[(6-Chloropyrid-3-yl)methyl] (cyclopropyl)amino}furan-2(5H)-on (M25.9) and 4-{[(6-Chloropyrid-3-yl)methyl](methyl)amino}furan-2 (5H)-on (M25.10);

(M26) various compounds: amidoflumet, benclothiaz, benzoximate, bifenazate, borax, bromopropylate, cyenopyrafen, cyflumetofen, chinomethionate, dicofol, fluoroacetate, pyridalyl, pyrifluquinazon, tartar emetic, sulfoxaflor, N—R'-2,2-dihalo-1-R''cyclo-propanecarboxamide-2-(2,6-dichloro-α,α,α-trifluoro-p-tolyl)hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R'' is hydrogen or methyl and R''' is methyl or ethyl, 4-But-2-ynyloxy-6-(3,5-dimethyl-piperidin-1-yl)-2-fluoro-pyrimidine (M26.1), Cyclopropaneacetic acid, 1,1'-[(3S,4R, 4aR,6S,6aS,12R,12aS,12bS)-4-[[(2-cyclopropylacetyl) oxy]methyl]-1,3,4,4a,5,6,6a,12,12a,12b-decahydro-[2-hydroxy-4,6a,12b-trimethyl-11-oxo-9-(3-pyridinyl)-2H,11H-naphtho[2,1-b]pyrano[3,4-e]pyran-3,6-diyl] ester (M26.2) and 8-(2-Cyclopropylmethoxy-4-trifluoromethyl-phenoxy)-3-(6-trifluoromethyl-pyridazin-3-yl)-3-aza-bicyclo[3.2.1]octane (M26.3).

The commercially available compounds described above may be found in The Pesticide Manual, 13th Edition, British Crop Protection Council (2003) among other publications.

Paraoxon and their preparation have been described in Farm Chemicals Handbook, Volume 88, Meister Publishing Company, 2001. Flupyrazofos has been described in Pesticide Science 54, 1988, p. 237-243 and in U.S. Pat. No. 4,822, 779. AKD 1022 and its preparation have been described in U.S. Pat. No. 6,300,348. The anthranilamides M22.1 to M22.6 have been described in WO 2008/72743 and WO 200872783 and M22.7 to M22.12 have been described in WO 2007/043677. The phthalamide M20.1 is known from WO 2007/101540. The alkynylether compound M26.1 is described in, for example, JP 2006131529. Organic sulfur compounds have been described in WO 2007/060839. The isoxazoline compounds M 21.1 to M21.8 have been described in, for example, WO 2005/085216, WO 2007/079162, WO 2007/026965, WO 2009/126668 and WO 2009/051956. The aminofuranone compounds M25.1 to M25.10 have been described in, for example, WO 2007/115644. The pyripyropene derivative M 26.2 has been described in WO 2008/66153 and WO 2008/108491. The pyridazin compound M26.3 has been described in JP 2008/115155. Malononitrile compounds as M23.1 and M23.2 have been described in WO 02/089579, WO 02/090320, WO 02/090321, WO 04/006677, WO 05/068423, WO 05/068432 and WO 05/063694.

Suitable fungicides which may be included in the compositions of the present include the following list of compounds ("N compounds"):

(N1) respiration Inhibitors:
(N1a) inhibitors of complex III at Qo site (e.g. strobilurins):
strobilurins: azoxystrobin, dimoxystrobin, enestroburin, fluoxastro-bin, kresoxim-methyl, meto-minostrobin, orysastrobin, picoxy-strobin, pyraclostrobin, pyrametostrobin, pyraoxystrobin, pyribencarb, trifloxystrobin, methyl (2-chloro-5[1-(3-methylbenzyl-oxy-imino)-ethyl]benzyl)-carbamate and 2 (2-(3-(2,6-di-chlorophenyl)-1-methyl-allylidene-aminooxy-methyl)-phenyl)-2-methoxyimino-N methyl-acetamide;

oxazolidinediones and imidazolinones: famoxadone, fenamidone;

(N1b) inhibitors of complex II (e.g. carboxamides)

carboxanilides: benodanil, bixafen, boscalid, carboxin, fen-furam, fenhexamid, fluopyram, flutolanil, furametpyr, isopyrazam, isotianil, mepronil, oxycarboxin, penflufen, penthiopyrad, sedaxane, tecloftalam, thifluz-amide, tiadinil, 2-amino-4 methyl-thiazole-5-carbox-anilide, N-(3',4',5' tri-fluoro-bi-phenyl-2 yl)-3-difluoro-methyl-1-methyl-1H-pyrazole-4 carboxamide, N-(4'-tri-fluoro-methyl-thiobi-phenyl-2-yl)-3 difluoromethyl-1-methyl-1H pyrazole-4-carbox-amide and N-(2-(1,3,3-trimethyl-butyl)-phenyl)-1,3-dimethyl-5 fluoro-1H-pyrazole-4 carbox-amide;

(N1c) inhibitors of complex III at Qi site:
cyazofamid, amisulbrom;

(N1d) other respiration inhibitors (complex I, uncouplers)
diflumetorim;
nitrophenyl derivates: binapacryl, dinobuton, dinocap, fluazinam, nitrothal-isopropyl, tecnazene;
ferimzone;
organometal compounds: fentin salts, such as fentinacetate, fentin chloride or fentin hydroxide;
ametoctradin;
silthiofam;

(N2) sterol biosynthesis inhibitors (SBI fungicides)

(N2a) C14 demethylase inhibitors (DMI fungicides, e.g. triazoles, imidazoles):

triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, paclobutrazole, penconazole, propiconazole, prothio-conazole, simeconazole, tebuconazole, tetraconazole, triadimefon, triadimenol, triticonazole, uniconazole;

imidazoles: imazalil, pefurazoate, oxpoconazole, prochloraz, triflumizole;

pyrimidines, pyridines and piperazines: fenarimol, nuarimol, pyrifenox, triforine;

(N2b) Delta 14-reductase inhibitors (Amines, e.g. morpholines, piperidines morpholines: aldimorph, dodemorph, dodemorph-acetate, fenpropimorph, tridemorph;
piperidines: fenpropidin, piperalin;
spiroketalamines: spiroxamine;

(N2c) inhibitors of 3-keto reductase
hydroxyanilides: fenhexamid;

(N3) nucleic acid synthesis inhibitors (N3a) RNA, DNA synthesis
phenylamides or acyl amino acid fungicides: benalaxyl, benalaxyl-M, kiralaxyl, metalaxyl, metalaxyl-M (mefenoxam), ofurace, oxadixyl;
isoxazoles and isothiazolones: hymexazole, octhilinone;

(N3b) DNA topisomerase inhibitors
oxolinic acid;

(N3c) nucleotide metabolism (e.g. adenosin-deaminase)
hydroxy(2-amino)-pyrimidines: bupirimate;

(N4) inhibitors of cell division and or cytoskeleton (N4a) tubulin inhibitors
benzimidazoles and thiophanates: benomyl, carbendazim, fuberidazole, thiabendazole, thiophanate-methyl;
triazolopyrimidines: 5-chloro-7 (4-methyl-piperidin-1-yl)-6-(2,4,6-trifluorophenyl)-[1,2,4]tri-azolo-[1,5a] pyrimidine (N4b) other cell division inhibitors
benzamides and phenyl acetamides: diethofencarb, ethaboxam, pencycuron, fluopicolide, zoxamide;

(N4C) actin inhibitors
benzophenones: metrafenone;

(N5) inhibitors of amino acid and protein synthesis (N5a) methionine synthesis inhibitors (aniline pyrimidines)
anilino-pyrimidines: cyprodinil, mepanipyrim, nitrapyrine, pyrimethanil;

(N5b) protein synthesis inhibitors (anilino-pyrimidines)
antibiotics: blasticidin-S, kasugamycin, kasugamycin hydrochloride-hydrate, mildiomycin, streptomycin, oxytetracyclin, polyoxine, validamycin A;

(N6) signal transduction inhibitors (N6a) MAP/Histidine kinase inhibitors (e.g. anilino-pyrimidines)
dicarboximides: fluoroimid, iprodione, procymidone, vinclozolin;
phenylpyrroles: fenpiclonil, fludioxonil;

(N6b) G protein inhibitors (quinolines)
quinolines: quinoxyfen;

(N7) lipid and membrane synthesis inhibitors (N7a) phospholipid biosynthesis inhibitors (e.g.)
organophosphorus compounds: edifenphos, iprobenfos, pyrazophos;
dithiolanes: isoprothiolane;

(N7b) lipid peroxidation
aromatic hydrocarbons: dicloran, quintozene, tecnazene, tolclofos-methyl, biphenyl, chloroneb, etridiazole;

(N7c) carboxyl acid amides (CAA fungicides)
cinnamic or mandelic acid amides: dimethomorph, flumorph, mandiproamid, pyrimorph;
valinamide carbamates: benthiavalicarb, iprovalicarb, pyribencarb, valifenalate and N-(1-(1-(4-cyano-phenyl)-ethanesulfonyl)-but-2-yl) carbamic acid-(4-fluorophenyl) ester;

(N7d) Compounds affecting cell membrane permeability and fatty acids
carbamates: propamocarb, propano-carb-hydrochlorid (N8) inhibitors with Multi Site Action (N8a) inorganic active substances
Bordeaux mixture, copper acetate, copper hydroxide, copper oxychloride, basic copper sulfate, sulfur;

(N8b) thio- and dithiocarbamates
ferbam, mancozeb, maneb, metam, methasulphocarb, metiram, propineb, thiram, zineb, ziram;

(N8c) organochlorine compounds (e.g. phthalimides, sulfamides, chloronitriles)
anilazine, chlorothalonil, captafol, captan, folpet, dichlofluanid, dichlorophen, flusulfamide, hexachlorobenzene, pentachlorphenole and its salts, phthalide, tolylfluanide, N-(4-chloro-2-nitro-phenyl)-N-ethyl-4-methyl-benzenesulfonamide;

(N8d) guanidines
  guanidine, dodine, dodine free base, guazatine, guazatine-acetate, iminoctadine, iminoctadine-triacetate, iminoctadine-tris(albesilate);
(N8e) ahtraquinones
  dithianon;
(N9) Cell wall synthesis inhibitors
(N9a) Inhibitors of glucan synthesis
  validamycin, polyoxin B;
(N9b) Melanin synthesis inhibitors
  pyroquilon, tricyclazole, carpropamide, dicyclomet, fenoxanil;
(N10) Plant defense inducers
(N10a) salicylic acid pathway
  acibenzolar-S-methyl;
(N 10b) others
  probenazole, isotianil, tiadinil, prohexadione-calcium;
  phosphonates: fosetyl, fosetyl-aluminum, phosphorous acid and its salts;
(N11) Unknown mode of action
  bronopol, chinomethionat, cyflufenamid, cymoxanil, dazomet, debacarb, diclomezine, difenzoquat, difenzoquat-methylsulfate, diphenylamin, flumetover, flusulfamide, flutianil, methasulfocarb, oxin-copper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N methyl formamidine, N' (4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethyl-silanyl-prop-oxy)-phenyl)-N-ethyl-N-methyl formamidine, N'-(5-difluoromethyl-2 methyl-4-(3-tri-methylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-meth-yl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, methoxy-acetic acid 6-tert-butyl-8-fluoro-2,3-dim-ethyl-quinolin-4-yl ester and N-Methyl-2-{1-[(5-methyl-3-trifluoro-methyl-1H-pyr-azol-1-yl)-acetyl]-pip-eri-din-4-yl}-N-[(1R)-1,2,3,4-tetrahydro-naphthalen-1-yl]-4-thi-azolecarboxamide, 3-[5-(4-chloro-phenyl)-2,3-dimethyl-isoxazolidin-3 yl]-pyridine, 3-[5-(4-methyl-phenyl)-2,3-dimethyl-isoxazolidin-3-yl]-pyridine, 5-amino-2-iso-propyl-3-oxo-4-ortho-tolyl-2,3-dihydro-pyrazole-1 carbo-thioic acid S-allyl ester, N-(6-methoxy-pyridin-3-yl)cyclopropanecarboxylic acid amide, 5-chloro-1 (4,6-dimethoxy-pyrimidin-2-yl)-2-methyl-1H-benzoimidazole, 2-(4-chloro-phenyl)-N-[4-(3,4-dimeth-oxy-phenyl)-isoxazol-5-yl]-2-prop-2-ynyloxy-acetamide;
(N 12) growth regulators
  abscisic acid, amidochlor, ancymidol, 6-benzylaminopurine, brassinolide, butralin, chlormequat (chlormequat chloride), choline chloride, cyclanilide, daminozide, dike-gulac, dimethipin, 2,6-dimethylpuridine, ethephon, flumetralin, flurprimidol, fluthi-acet, forchlorfenuron, gibberellic acid, inabenfide, indole-3-acetic acid, maleic hydrazide, mefluidide, mepiquat (mepiquat chloride), naphthaleneacetic acid, N 6 benzyladenine, paclobutrazol, prohexadione (prohexadione-calcium), prohydrojasmon, thidiazuron, triapenthenol, tributyl phosphorotrithioate, 2,3,5 tri iodobenzoic acid, trinexapac-ethyl and uniconazole;
(N13) biological control agents
  antifungal biocontrol agents: *Bacillus substilis* strain with NRRL No. B-21661 (e.g. RHAPSODY®, SERENADE® MAX and SERENADE® ASO from AgraQuest, Inc., USA.), *Bacillus pumilus* strain with NRRL No. B-30087 (e.g. SONATA® and BALLAD® Plus from AgraQuest, Inc., USA), Ulocladium oudemansii (e.g. the product BOTRY-ZEN from BotriZen Ltd., New Zealand), Chitosan (e.g. ARMOUR-ZEN from BotriZen Ltd., New Zealand).

Suitable herbicides that may be incorporated into the pesticide compositions of the present disclosure include the compounds listed below ("P Compounds")

(P1) acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;
(P2) amino acid derivatives: bilanafos, glyphosate, glufosinate, sulfosate;
(P3) aryloxyphenoxypropionates: clodinafop, cyhalofop-butyl, fenoxaprop, fluazifop, haloxyfop, metamifop, propaquizafop, quizalofop, quizalofop-P-tefuryl;
(P4) Bipyridyls: diquat, paraquat;
(P5) (thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;
(P6) cyclohexanediones: butroxydim, clethodim, cycloxydim, profoxydim, sethoxydim, tepraloxydim, tralkoxydim;
(P7) dinitroanilines: benfluralin, ethalfluralin, oryzalin, pendimethalin, prodiamine, trifluralin;
(P8) diphenyl ethers: acifluorfen, aclonifen, bifenox, diclofop, ethoxyfen, fomesafen, lactofen, oxyfluorfen;
(P9) hydroxybenzonitriles: bomoxynil, dichlobenil, ioxynil;
(P10) imidazolinones: imazamethabenz, imazamox, imazapic, imazapyr, imazaquin, imazethapyr;
(P11) phenoxy acetic acids: clomeprop, 2,4-dichlorophenoxyacetic acid (2,4-D), 2,4-DB, dichlorprop, MCPA, MCPA-thioethyl, MCPB, Mecoprop;
(P12) pyrazines: chloridazon, flufenpyr-ethyl, fluthiacet, norflurazon, pyridate;
(P13) pyridines: aminopyralid, clopyralid, diflufenican, dithiopyr, fluridone, fluoroxypyr, picloram, picolinafen, thiazopyr;
(P14) sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1 ((2-chloro-6-propyl-imidazo[1,2-b]pyridazin-3-yl)sulfonyl)-3-(4,6-dimethoxy-pyrimidin-2-yl)urea;
(P15) triazines: ametryn, atrazine, cyanazine, dimethametryn, ethiozin, hexazinone, metamitron, metribuzin, prometryn, simazine, terbuthylazine, terbutryn, triaziflam;

(P16) ureas: chlorotoluron, daimuron, diuron, fluometuron, isoproturon, linuron, metha-benzthiazuron, tebuthiuron;

(P17) other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;

(P18) others: amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidon-ethlyl, chlorthal, cinmethylin, clomazone, cumyluron, cyprosulfamide, dicamba, difenzoquat, diflufenzopyr, *Drechslera monoceras*, endothal, ethofumesate, etobenzanid, fenoxasulfone, fentrazamide, flumiclorac-pentyl, flumioxazin, flupoxam, fluorochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester.

Typically the pesticide of the present disclosure is a particulate that is suspended in the pesticide composition and, particularly, within and throughout the diluent of the composition. Generally, any of the compounds listed above may be a particulate in the composition. For instance, the active material may be in a crystallized and/or powdered form (e.g., relatively pure solid particulate material may be used) and may be dispersed throughout a diluent in which the active is insoluble or at least partially insoluble. The composition of the present disclosure is generally not a emulsion; rather, after packaging, the composition generally is a colloidal dispersion and, after application, is a colloidal foam. In this regard, it should be understood that use of the term "particulate" herein does not include liquid or particulate materials that have been microencapsulated and suspended in the pesticide composition. Pesticide compositions containing microencapsulated pesticides may have lesser activities then formulations containing non-encapsulated pesticides and are generally more expensive to produce.

In certain embodiments, the particulate pesticide is fipronil (synonymously "fluocyanobenpyrazole"). Fipronil is known chemically as (±)-5-amino-1-(2,6-dichloro-α,α,α-trifluoro-p-tolyl)-4-trifluoromethylsulfinylpyrazole-3-carbonitrile and is available in technical grades or in commercial concentrates such as TERMIDOR® SC. The structure of fipronil is illustrated in Formula (I) below, 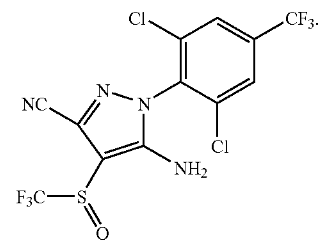 (I)

Fipronil has been found effective in treatment of many pests including, for example, termites, ants, beetles, cockroaches, fleas, ticks, mole crickets, thrips, rootworms and weevils. Generally, fipronil may be toxic to termites at a dose of 2 nanograms per termite and may be toxic to ants at a dose of about 1 nanogram per ant.

When fipronil is used at the pesticide, the average nominal diameter of the particulate fipronil may be less than about 50 μm and, in other embodiments, less than about 25 μm, less than 10 μm or even less than 5 μm. In various other embodiments, the average nominal diameter of the particulate fipronil is from about 0.5 μm to about 25 μm, from about 0.5 μm to about 10 μm or from about 1 μm to about 5 μm. Due to the small particle size of fipronil, the pesticide composition appears homogeneous to the naked eye before and after application. Smaller particle sizes are also preferred as smaller particles are less likely to settle out during storage of the composition. Suitable commercially available sources of fipronil include, for example, technical grade fipronil and TERMIDOR® SC.

The amount of pesticide utilized in the pesticide composition may vary depending on the intended use of the composition including, for example, the pests intended for control. In one embodiment, a pest is contacted with the pesticide composition in a pesticidally effective amount. For purposes of the present disclosure, a "pesticidally effective amount" of the composition includes amounts that repel the pest and may include, in another embodiment, amounts of the composition that kill the pest. When fipronil is used as the pesticide, the composition comprises at least about 0.005% by weight particulate fipronil and, in other embodiments, at least about 0.01%, at least about 0.04%, at least about 0.1% or even at least about 0.5% by weight particulate fipronil. In various other embodiments, the composition comprises from about 0.005% to about 3% by weight particulate fipronil, from about 0.005% to about 1% by weight particulate fipronil or from about 0.01% to about 1% by weight particulate fipronil.

When a pesticide other than fipronil is utilized (such as any of the compounds listed above such as chlorfenapyr, metaflumizone, chloratraniprole, idoxacarb and α-cypermethrin), the composition comprises at least about 0.005% by weight pesticide and, in other embodiments, at least about 0.01%, at least about 0.1% or even at least about 1% by weight pesticide.

As described above, the particulate pesticide may be suspended in the diluent of the pesticide composition. In one embodiment, the diluent is water. Generally, the composition comprises at least about 50% diluent by weight and, in other embodiments, comprises at least about 75%, at least about 85% or even at least about 90% diluent by weight of the composition.

In some embodiments, the pesticide composition comprises a thickening agent. Generally, thickening agents are utilized to increase the viscosity of the composition and to impart desirable fluid properties to the composition. Generally, natural or synthetic polysaccharide gums and some clays (e.g., bentonite clay) may be used as a thickening agent. Among suitable thickening agents are xanthan gum, guar gum, gum arabic, alginin, gum tragacanth, sodium alginate and mixtures thereof. In one embodiment, the thickening agent is xanthan gum. The composition may include at least about 0.01% thickening agent by weight and, in another embodiment, at least about 0.05% thickening agent by weight. In various embodiments, the pesticide composition includes from about 0.05% to about 1% thickening agent by weight of the composition, from about 0.08% to about 0.5% or from about 0.08% to about 0.15% thickening agent by weight of the composition. The composition may include more than one thickening agent with the total amount of thickening agents corresponding to the previously listed amounts.

The composition may also include a foaming stabilizer (or synonymously "breaking agent"). Generally, the foaming stabilizer regulates the length of time the composition remains in a foam phase after it is applied with relatively higher amounts of foaming stabilizer generally corresponding to longer periods of time the composition remains as a foam and vice versa. Generally, the foam composition will disintegrate into a liquid composition over time. The foam stabilizer may slow the rate at which the foam disintegrates. The composition may include at least about 0.01% foam stabilizer by weight and, in another embodiment, at least about 0.05% foam stabilizer by weight. In various embodiments, the pesticide composition includes from about 0.05% to about 1% foam stabilizer by weight of the composition, from about 0.08% to about 0.5% or from about 0.08% to about 0.15% foam stabilizer by weight of the composition.

In several embodiments of the present disclosure, the foam stabilizer and the thickening agent are the same, i.e., one compound or series of compounds act as a thickening agent and foam stabilizer. In one embodiment, the foam stabilizer and thickening agent are a compound selected from the group consisting of xanthan gum, guar gum, gum arabic, alginin, gum tragacanth, sodium alginate and mixtures thereof. In another embodiment, the foam stabilizer and thickening agent are xantham gum. In embodiments where the thickening agent and the foam stabilizer are the same compound or series of compounds, the compound(s) may be present in the composition in the amounts listed above relating to the thickening agent or the foam stabilizer.

In one embodiment, the composition is capable of remaining in a foam phase for at least about 30 minutes after application. Such compositions may generically be referred to as "slow-breaking." This is desirable when the composition is to be applied to hard-to-reach voids, crevices, spaces or surfaces typically found on or near the exterior or interior of residential or commercial structures such as, for example, voids within cabinetry, inside of wood-based-structural supports, voids within bricks, retaining walls (particularly wood-based structures such as railroad ties) and voids or crevices that are sub-grade. The composition is generally in the "foam phase" when at least 5% by volume of the initial volume of the applied composition may be characterized by a "froth" or "foam" consistency.

In some embodiments, it is desirable for the composition to be capable of remaining in a foam phase for at least about 30 minutes after application in order to increase the distribution and bioavailability of the toxic pesticide within the target application site. By remaining in the foam phase, the composition remains suspended within the treated site longer which allows for particulate pesticide to remain evenly dispersed within or across the treated site. This is particularly advantageous for the treatment of interior or structural voids. The longer the foam remains intact the less moisture that is available to run off or flow out of the treatment area and carry toxic compounds into surrounding areas that may not be protected or allow for unintentional contact by humans or animals. Maintaining the distribution of the particulate pesticide across the entire treated area also eliminates the creation of spots or zones of pesticide concentrations that are too low to affect the target insect or other arthropod while at the same time creating spots or zones where the concentration of the pesticide may be sufficiently great resulting in insects or other arthropods being repelled.

In one embodiment, the composition is capable of remaining in the foam phase for at least about 30 minutes after application. In various other embodiments, the composition is capable of remaining in a foam phase for at least about 1 hour after application, at least about 2 hours after application or even at least about 4 hours after application. In various other embodiments, the composition is capable of remaining in a foam phase for from about 10 minutes to about 10 hours after application or from about 30 minutes to about 5 hours after application.

In other embodiments, it is desirable for the pesticide composition to be capable of being in a foam phase after application but remain in the foam phase for less than about 10 minutes after application. Such compositions may generically be referred to as "fast-breaking." Generally, this is desirable when the pesticide composition is to be applied outdoors such as, for example, application to exterior surfaces exposed to typical weather conditions. The advantage of fast-breaking foams is that the individual applying the composition can easily view the foamed area that has been treated, avoiding over application or possible treatment of unintended areas, yet the foam disintegrates relatively quickly to promote the drying of the treatment area which reduces the potential for unintended dislodging or transfer of the wet material by means of humans or animal traffic within the treated area following application.

In one embodiment, the composition after applied is capable of remaining in the foam phase for less than about 10 minutes after application. The pesticide composition may be capable of being in a foam phase after application and remains in the foam phase for less than about 5 minutes after application and, in other embodiments, for less than about 2 minutes, for less than about 1 minute, for less than about 30 seconds and even less than about 15 seconds after application. In some embodiments, the pesticide composition foams for from about 1 second to about 5 minutes, for from about 1 second to about 1 minute, for from about 5 seconds to about 1 minute or from about 5 seconds to about 30 seconds after application. The rate at which the foam breaks may generally be controlled by selecting the amount of surfactant included in the composition with higher amounts of surfactant corresponding to lower foam breaking rates. The rate may also be controlled by selection of appropriate wands and/or nozzles. The length of time the composition foams may also be increased by using hydrocarbon propellants or by using thickening agents such as, for example, xanthan gum.

The fast-breaking foam broadly acts as a visual indicator (e.g., as opposed to conventional compositions that are applied as a liquid which is difficult to see once applied, particularly to a ground surface) to allow the individual applying the composition to readily see areas that have been treated, thus reducing the risk of over application or possible treatment of unintended areas. The foam breaks down or disintegrates relatively quickly to promote the drying of the treatment area, thus reducing the potential for unintended dislodging or transfer of the wet material by humans, animal traffic and/or wind following application. There is also no undesired or unsightly visual indicator remaining once the treatment is completed.

While in some embodiments the composition is configured to deliver a visual indicator in the form of a foam, it is understood that other visual indicators instead, or additionally, may be provided in the composition without departing from the scope of this disclosure. For example, in some embodiments the composition may be deliverable as either a liquid or a foam (or a powder) and may include a visual indicator in the form of a colorant to allow the person applying the treatment to track where applications have been made. In particular such embodiments the colorant may suitably fade or disappear shortly after application (e.g., within the same timing requirements as the fast-breaking foam discussed above).

Generally, the pesticide composition expands as it is applied and transitions to the foam phase. The foamable pesticide composition may be characterized by a foam expansion ratio of at least about 2:1. In other embodiments, the composition is characterized by a foam expansion ratio of at least about 10:1 or even about 25:1. In various other embodiments, the ready-to-use foamable pesticide composition is characterized by a foam expansion ratio of from about 2:1 to about 60:1 or from about 10:1 to about 40:1.

The pesticide composition may also contain a surfactant system. Generally, the surfactant system may cause the composition to be in a foam phase after applied. The composition may contain at least about 0.05% surfactant system by weight of the composition and, in other embodiments, at least about 0.15%, or even at least about 0.25% surfactant system by weight of the composition. In other various embodiments, the pesticide composition includes from about 0.05% to about 0.45% surfactant system by weight of the composition or from about 0.1% to about 0.4% surfactant system by weight of the composition.

The surfactant system may include synthetic or natural surfactants and a plurality of surfactants may be included in the system. Suitable surfactants include, for example, fatty acid soaps. The surfactant or surfactants may be chosen from potassium coconut fatty acid, sodium lauryl sulfate, sodium laureth sulfate, alpha olefin sulfonates and mixtures thereof. Suitable alpha olefin sulfonates include C14 to C16 olefin sulfonates and mixtures thereof. In a particular embodiment, the surfactant system comprises potassium coconut fatty acid and an alpha olefin sulfonate.

The surfactant system may include at least about 0.05% by weight coconut fatty acid and, in other embodiments, includes at least about 0.1% by weight coconut fatty acid or at least about 0.15% by weight coconut fatty acid. In various other embodiments, the surfactant system comprises from about 0.05% to about 1% by weight coconut fatty acid or from about 0.05% to about 0.5% by weight coconut fatty acid.

The surfactant system may include at least about 0.01% by weight C14 to C16 olefin sulfonates, at least about 0.05% by weight C14 to C16 olefin sulfonates or even at least about 0.09% by weight C14 to C16 olefin sulfonates. In various other embodiments, the surfactant system comprises from about 0.01% to about 0.5% by weight C14 to C16 olefin sulfonates, from about 0.01% to about 0.2% by weight C14 to C16 olefin sulfonates. The total amount of surfactants within the surfactant system may be at least about 0.05% surfactants by weight of the composition, at least about 0.1%, at least about 0.25% or even at least about 0.4% surfactants by weight of the composition.

The ready-to-use pesticide compositions of embodiments of the present disclosure may also include a preservative compound. The preservative compound acts to prevent biological breakdown of the composition by microorganisms such as bacteria and fungi. Suitable preservatives include butylated hydroxytoluene, butylated hydroxyanisole, tert-butylhydroquinone, propyl gallate, parabens, sulfur dioxide, ethylenediaminetetraacetic acid, sodium benzoate and mixtures thereof. In one embodiment, the preservative is sodium benzoate. The total amount of preservative compounds in the composition may be at least about 0.01% by weight of the composition and, in other embodiments, at least about 0.1% by weight of the composition or even at least about 0.15% by weight of the composition. In various other embodiments, the total amount of preservative compounds in the composition is from about 0.01% to about 0.40% by weight of the composition or from about 0.1% to about 0.40% by weight of the composition.

When fipronil is used as the pesticide, the pesticide composition may also contain a fipronil stabilizer compound. Such compounds prevent or slow the rate at which fipronil breaks down and loses its pesticidal effectiveness. Generally, the stabilizer compound maintains a pH of the composition below 8 at which fipronil is more active. The fipronil stabilizer compound may be an organic acid. In one embodiment, the fipronil stabilizer compound is citric acid. The total amount of fipronil stabilizer compounds in the composition may be at least about 0.005% by weight of the composition. In various other embodiments, the total amount of fipronil stabilizer compounds in the composition is from about 0.005% to about 1% by weight of the composition, from about 0.005% to about 0.1% by weight of the composition or from about 0.005% to about 0.05% by weight of the composition.

As packaged, the composition may also include propellants which pressurize the storage container and which create foaming action upon application of the composition. The total amount of propellants in the pesticide composition may be at least about 1% by weight of the composition. Suitable propellants include, for example, propane, isobutane, dimethyl ether, difluoroethane, tetrafluoroethane, carbon dioxide and mixtures thereof.

In one embodiment, the composition is characterized by a pH of from about 6.5 to about 8 and, in another embodiment, by a pH of from about 7 to about 7.25. If the composition has a pH below about 6.5 to about 7, the container housing the composition may corrode with lower pH's corresponding to a higher rate of corrosion. Also, fipronil tends to be more active at a pH below about 8. The composition may be characterized by a pH other than those listed without departing from the scope of the present disclosure.

Generally, the composition is prepared by mixing all ingredients other than propellants in their relative proportions and, in one embodiment, as done in Example 1 below. Citric acid may be mixed until the desired pH is reached. All mixing can be done at room temperature. Once mixed, the composition is added to a suitable container and a propellant may be added if desired.

Generally, the composition is applied to a target void, crevice or surface. Once applied, the composition may be in a foam phase. Target pests may be contacted with the foam phase as it is applied or come into contact with the foam after applied. Further, the foam composition may disintegrate into a liquid composition and the pest may contact the composition while the composition is in a liquid phase. The liquid may evaporate to form dried particulate pesticide residue on the locus of application.

Pesticide Applicator

Embodiments of the ready-to-use foamable pesticide composition described above may be incorporated into a pesticide applicator utilized for applying pesticides such as fipronil to pests. Generally, the applicator may include a container and a pesticide composition within the container. The pesticide composition may optionally include a diluent, particulate pesticide (e.g., fipronil) suspended in the diluent, a thickening agent and a surfactant system comprising at least one surfactant. Other optional additives include foam stabilizers (which may also serve as thickening agents), preservatives, fipronil stabilizers and/or propellants as described above.

Suitable containers may be constructed of, for example, three-piece tinplate, aluminum and PET-lined steel containers. The pesticide composition may be pressurized within the container by addition of a propellant. The total amount of propellants in the pesticide composition may be at least about 1% by weight of the composition and, in another embodiment, is at least about 5% by weight of the composition. The total amount of propellants in the pesticide composition may be from about 1% to about 12% by weight or even about 3% to about 10% by weight. As stated above, suitable propellants include propane, isobutane, dimethyl ether, difluoroethane, tetrafluoroethane, carbon dioxide and mixtures thereof. In one embodiment, the composition comprises propane and isobutane as propellants. The propellants may be compressed gases, soluble gases or liquefied gases. In one embodiment, the propellant is a liquefied hydrocarbon selected from the group consisting of propane, isobutane, dimethyl ether, difluoroethane and tetrafluoroethane.

Referring now to FIG. 1, an embodiment of a pesticide applicator for storage and application of pesticide compositions of embodiments of the present disclosure is illustrated. The applicator 20 includes a container 25. The applicator 20 includes a pesticide composition (not shown) within the container 25 as described above. In one embodiment, the pesticide composition includes a solvent, a pesticide dissolved in the solvent and an attractant.

The pesticide applicator 20 includes a cap 28 which houses a valve (not shown). An actuator (not shown but generally located within or as part of the cap at 32) is connected to the valve for regulating the flow of the pesticide composition from the container 25. The actuator is sized and shaped for activation by a pressing force that may be provided by a human finger. The applicator 20 includes an exhaust port 38 that is fluidly connected to the container 25 upon activation of the actuator (i.e., opening of the valve). An injector tip 35 is fluidly connected to the exhaust port through a tube 40.

For purposes of the present disclosure, "fluidly connected" is meant to include, for example, arrangements in which a fluid is capable of flowing within after application of a differential fluid driving force such as, for example, a pressure difference.

Figure 2:
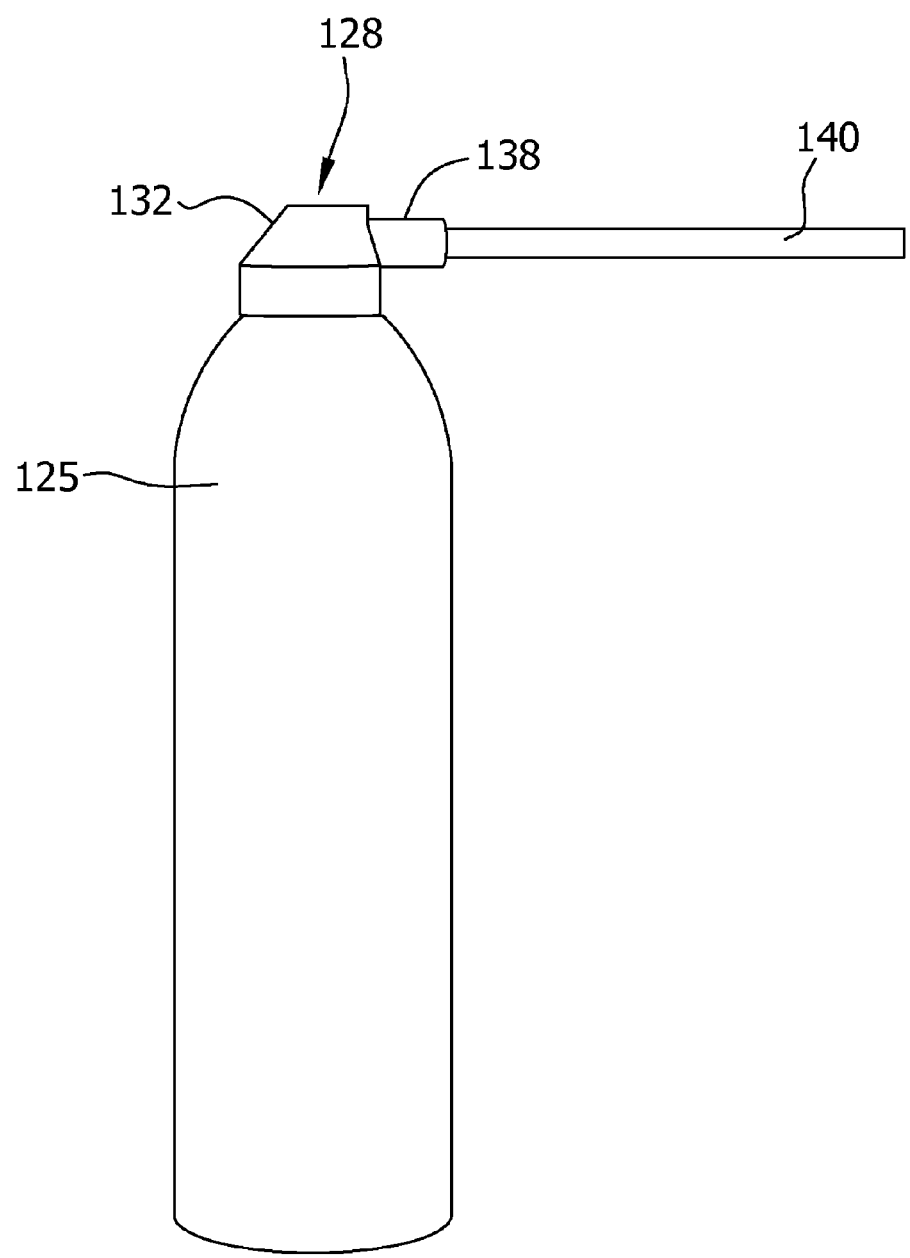
FIG. 2 is a front-side view of a pesticide applicator according to a second embodiment of the present disclosure.

A second embodiment of an applicator of the present disclosure is illustrated in FIG. 2. The pesticide applicator 120 is similar to the applicator 20 of FIG. 1 however the applicator 120 does not include an injector tip. Also the tube 140 may be more rigid such that the user does not need to grasp and direct the tube to the area of application but rather can direct the direction of dispersion of the composition with the same hand used to activate the actuator. In one embodiment, the applicator does not include a tube 140 and the composition is applied through the exhaust port 138.

Figure 3:
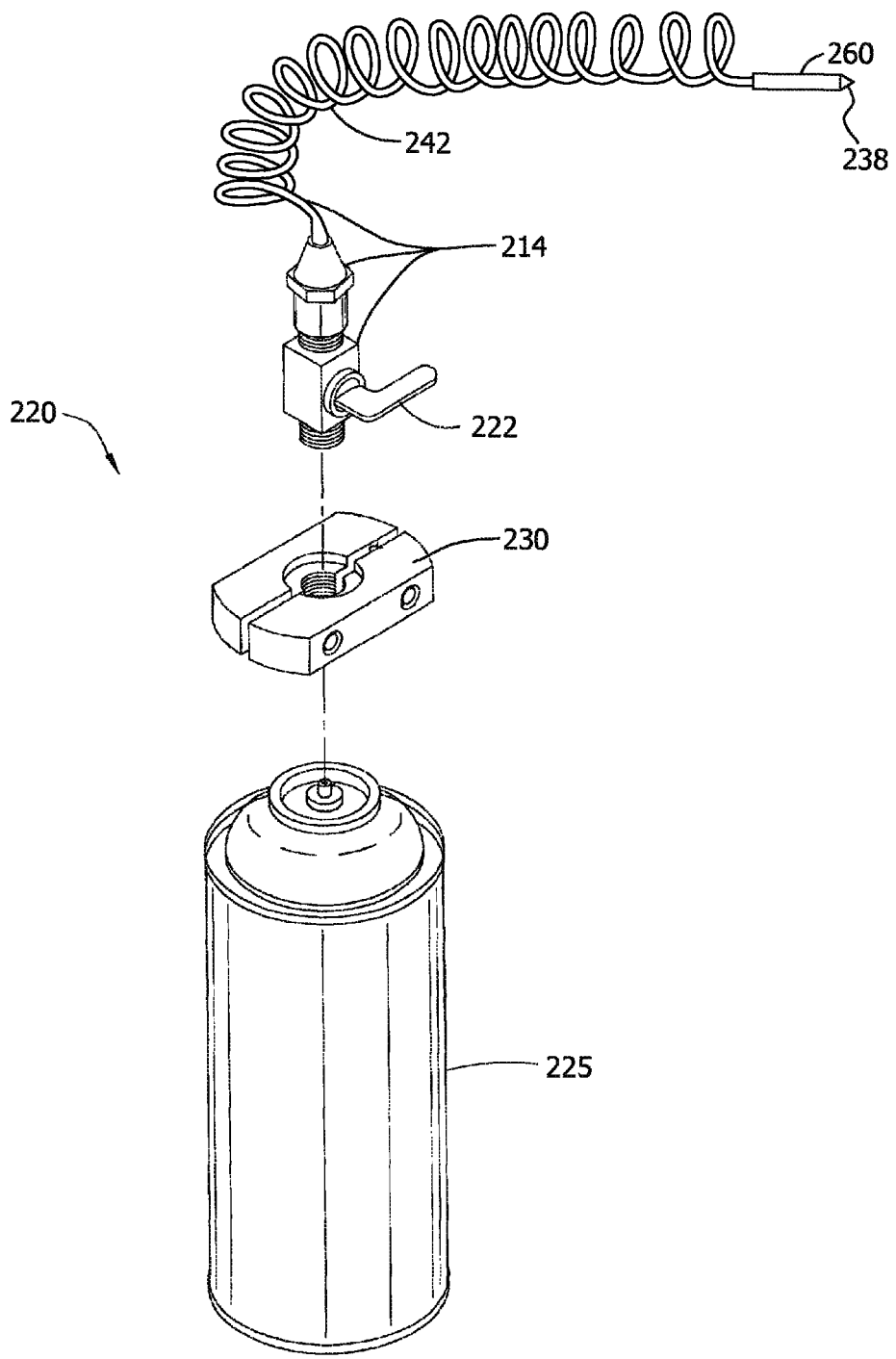
FIG. 3 is an exploded perspective view of a pesticide applicator according to a third embodiment of the present disclosure.

A third embodiment of an applicator of the present disclosure is illustrated in FIG. 3. The pesticide applicator 220 includes a container 225 (e.g., aerosol can) with an internal valve (not shown), an adaptor clamp 230 and a delivery system 214 as disclosed in U.S. Pat. No. 6,840,461 which is incorporated herein for all relevant and consistent purposes. As shown, the delivery system includes a coiled hose 242 (which optionally may or may not be extendible), wand 260 and exhaust port 238; however, it should be understood that other delivery systems may be used without departing from the scope of the present disclosure. The composition is dispensed upon activation of the actuator 222. Suitable wands (including wands used with other containers and applicators) may be a variety of lengths (e.g., about 10 in to about 25 inches). The delivery system (e.g., assembly gun) may be obtained commercially from B&G Equipment Company (Jackson, Ga.) and the wand may be obtained from Spraying Systems Company (Wheaton, Ill.). A suitable nozzle for use in perimeter applications (i.e., fast-breaking foams) is a TJet 650033 nozzle. As appreciated by those of skill in the art, the nozzle may be selected to influence or control the amount of time the foam remains in the foam-phase. Containers other than aerosol cans as shown in FIG. 3 may be used without departing from the scope of the present disclosure.

In another embodiment, the applicator includes a pump that is actuated by hand. A suitable pump spraying apparatus is illustrated and described in U.S. Pat. No. 6,415,956 which is incorporated herein for all relevant and consistent purposes. In another embodiment, the pump is electrically powered. The pump may pull the composition into a chamber and blow the composition out of a tube similar to the tube 140 of FIG. 2.

Before application of the composition it may be desirable to shake the applicator 20 so as to thoroughly mix the ingredients. In one embodiment, a small object is within the container such as, for example, a ¼ inch (6.4 mm) stainless steel ball. The object acts to accelerate the mixing of the ingredients.

Generally, the pesticide applicator may be used to control pests by dispensing the pesticide composition from the container and applying the composition to the target surface. The composition may be dispensed by, for example, applying a downward pressing force to the actuator of the applicator illustrated in FIGS. 1-3.

Methods for Controlling Pests

In one embodiment of the present disclosure, a method for controlling pests includes contacting a pest with a pesticidally effective amount of a composition comprising a diluent, particulate suspended in the diluent, a thickening agent and a surfactant system comprising at least one surfactant as described above. Other optional additives include foam stabilizers (which may also serve as thickening agents), preservatives, fipronil stabilizers and/or propellants as described above.

The composition may be applied to a target surface (void, space, crevice, etc.) and the composition may be in a foam phase after application. The pest may contact the composition while the composition is in the foam phase or the foam may disintegrate into a liquid composition and the pest contacts the composition while the composition is in a liquid phase. In one embodiment, the composition dries to leave behind dried particulate pesticide and the pest contacts the dried particulate pesticide.

The pesticide composition is well suited for application to the exterior of commercial or residential structures and in some embodiments for application interior of such structures as well. For example, in one embodiment of a method for controlling pests, a suitable applicator such as an applicator described above and is used to apply the composition to a target surface, such as the ground and/or exterior surface of a building structure, landscaping materials, and/or about any outdoor area (e.g., a garden area, a treed area, wooden fence posts, etc.). The composition is suitably applied in a predetermined pattern or at least an orderly or sequential pattern (e.g., along a circumferential path around a building structure) along a path of treatment. For example, in one embodiment, the composition may be applied in sequential, side-by-side rows that are normal to or otherwise not parallel to the path of treatment. In other embodiments, the composition may be applied in a single continuous line along the path of treatment, or intermittent, generally end-facing-end lines along the path of treatment.

During application, the visual indicator provided by the fast-breaking foaming-action of the composition allows the individual applying the composition to readily and temporarily determine by visible inspection where the composition has been applied and where next to apply the composition to facilitate complete coverage of the target surface without over-application of the composition.

In embodiments wherein the pesticide is toxic to arthropods such as ants and termites, perimeter application ensures that pests which cross the pesticide barrier contact the pesticide and are deterred or killed before or upon entry into the structure. In embodiments wherein the pesticide is a repellant to arthropods, the barrier acts to keep pests from crossing the barrier and entering the structure. Suitable pesticides may be toxic and/or repellant. In some embodiments, the composition includes more than one pesticide compound and, optionally, one compound is that repellant and one compound that is toxic to arthropods.

In some embodiments, the pest contacts the active pesticide upon application of the composition. It should be understood that contact between the pest and the pesticide composition may be caused by application of the composition in a space occupied by the pest or by the pest moving from one location to a location in which the composition has been applied. For purposes of the present application, the phrases "contacting a pest with the composition," "pest contacts the composition," "pest is contacted with the composition" and the like are interchangeable and generally refer to contact between the composition and the pest and do not infer translocation of either the pest or composition.

In some embodiments, the pest does not contact the pesticide composition until after about 1 minute after application, until after about 5 minutes or even until after about 30 minutes after application. Generally, the pesticide composition maintains its activity such that it is suitable for the pest to not contact the composition until after about 1 hour after application, until after about 12 hours after application, until after about 1 day after application, until after about 3 days after application or even until after about 7 days or more after application.

The amount of foaming agent (e.g., surfactant) in the pesticide composition may be selected to cause the composition to remain in the foam phase for a minimum target time or, as in another embodiment, a maximum target time. Alternatively, the applicator may be selected to cause the composition to remain in the foam phase for a desired target time. In certain embodiments where a minimum time the composition remains in the foam phase is desired, the composition may remain in a foam phase for at least about 30 minutes after application, for at least about 1 hour or even for at least about 2 hours after application. In various other embodiments, the composition remains in a foam phase for from about 10 minutes to about 10 hours after application or for from about 30 minutes to about 5 hours after application. In certain embodiments where a maximum time the composition remains in the foam phase is desired, the composition may remain in a foam phase for less than about 10 minutes after application, for less than about 5 minutes, for less than about 2 minutes, for less than about 1 minute, for less than about 30 seconds or even less than about 15 seconds after application. In some embodiments, the pesticide composition remains in the foam phase for from about 1 second to about 5 minutes, for from about 1 second to about 1 minute, for from about 5 seconds to about 1 minute or from about 5 seconds to about 30 seconds after application.

In this manner, the foam remains visible for a sufficient time such that the person applying the composition may use the foam as a guide to determine which areas have been treated and which have not, but allows the foam to break in a sufficiently short time so that the foam does not remain publicly visible after the person applying the composition is finished with the application process or at least within a short period thereafter. Fast-breaking foams also reduce the likelihood of the foam blowing away in the wind and reduce the amount of foam that collects on the exhaust port of the dispensing device.

While compositions, applicators and methods of embodiments of the present disclosure are generally described as containing a diluent with a particulate pesticide suspended therein, it should be understood that in certain embodiments, the foamable pesticide composition includes a solvent, a pesticide dissolved in the solvent, a thickening agent and a surfactant system comprising at least one surfactant. In certain embodiments, the solvent is water. Other optional additives include foam stabilizers (which may also serve as thickening agents), preservatives and/or propellants as described above.

While compositions, applicators and methods of embodiments of the present disclosure are generally described with reference to fipronil or other pesticides, it should be understood that these embodiments may optionally include other pesticides in combination or in place of these compound. Additional materials that may be included in the pesticide compositions of the present disclosure include essential oils or plant extracts such as spearmint, peppermint, clove, geraniol, wintergreen, lemongrass, thyme, and mixtures thereof.

Generally, the ready-to-use pesticide compositions, pesticide applicators and methods for controlling pests of embodiments of the present disclosure are suitable for treatment and control of pest populations generally. In one embodiment, the pest is an arthropod and, in another embodiment, is an insect. The target pest may be selected from the group consisting of termites, ants, cockroaches, beetles, earwigs, silverfish, crickets, spiders, centipedes, flies, mosquitoes, gnats, moths, wasps, hornets, bees, centipedes, millipedes, scorpions, pillbugs, sowbugs and the like. In one embodiment, the pest is a termite and, in another embodiment, the pest is an ant.

EXAMPLES

Example 1

Preparation of a Foamable Pesticide Composition that Includes Suspended Technical Grade Particulate Fipronil Deionized water was weighed out into a mixing vessel. Sodium benzoate (4.33 g; Emerald Kalama Chemical; Kalama, Wash.) was mixed into the water until dissolved. In a separate vessel a mixture of C14 to C16 olefin sulfonates sold under the brand name BIO-TERGE AS-40 (6.49 g with about 39% being active sulfonates; Stepan Company; Northfield, Ill.) was mixed with potassium coconut fatty acid (4.33 g; Derrick Soap Products; St. Louis, Mo.) and an amount of deionized water. Particulate fipronil (1.46 g with about 88.75% active fipronil; BASF; Germany) was added to the second vessel with caution to prevent dusting of fipronil. Xanthan gum sold under the brand name "Ticaxan Rapid-2 (2.16 g; Tic Gums; White Marsh, Md.) was added to the first vessel while mixing. After the first mixture was fully thickened the second mixture was added to the first mixture. The total amount of water added to the solution was 1982.92 g. Citric acid (0.24 g; ADM; Decatur, Ill.) was added to adjust the pH to between 7 and 7.25.

The composition appeared as a slightly hazy liquid after preparation and had a viscosity between about 50 to 1500 cps.

The mixture was added to a nickel tinplate DOT 2Q quality container (22.6 fl. oz. (0.668 liter)) lined with polyethylene terephthalate. The container included an exhaust valve and was activated by an actuator. The container exhausted into a tube that terminated in an injector tip. A first propellant sold under the brand name A-46 (26 g; Diversified CPC; Channahon, Ill.) that is a mixture of propane and isobutane (15.2% propane, 84.8% isobutane) and a second propellant that is propane and sold under the brand name A-108 (12.6 g; Diversified CPC; Channahon, Ill.) were added to the composition within the container. The two compositions were added in a ratio that generally matches the vapor pressure of an A-70 composition.

A foaming actuator was attached. The composition produced a consistent foam that appeared homogeneous. The relative proportions of all ingredients are shown in Table 1 below.

TABLE 1

Relative proportions of ingredients used to prepare the pesticide composition of Example 1.

| Component | Inclusion (wt %) |
|---|---|
| Particulate Fipronil | 0.0676 |
| | (0.0600 active) |
| Sodium Benzoate | 0.2000 |
| Xanthan Gum | 0.1000 |
| C14 to C16 Olefin Sulfonates | 0.3000 |
| | (0.1173 active) |
| Potassium Coconut Fatty Acid | 0.200 |
| Citric Acid | 0.0110 |
| Water | 91.6213 |
| A-46 (15.2% propane, 84.8% isobutane) | 5.0483 |
| A-108 (100% propane) | 2.4518 |

Example 2

Preparation of a Foamable Pesticide Composition that Includes Suspended Particulate Fipronil Obtained from TERMIDOR® SC A foamable pesticide composition containing suspended fipronil was prepared; however, unlike Example 1 which used technical grade fipronil, the source of fipronil in Example 2 was TERMIDOR® SC. It was found that TERMIDOR® SC contained fipronil in a smaller particle size that was less likely to settle out during storage of the composition.

Deionized water (2955.18 g) was weighed out into a mixing vessel. Sodium benzoate (6.49 g; Emerald Kalama Chemical; Kalama, Wash.) was mixed into the water until dissolved. Xanthan gum sold under the brand name "Ticaxan Rapid-2 (3.25 g; Tic Gums; White Marsh, Md.) was added to the first vessel while mixing. After the xanthan gum thickened the mixture, C14 to C16 olefin sulfonates sold under the brand name BIO-TERGE AS-40 (9.74 g with about 39% being active sulfonates; Stepan Company; Northfield, Ill.) and potassium coconut fatty acid (6.49 g; Derrick Soap Products; St. Louis, Mo.) were mixed in the composition. Particulate fipronil sold under the brand name TERMIDOR® SC (21.40 g with about 9.10% active fipronil; BASF; Germany) was mixed in the composition. Citric acid (0.36 g; Tate & Lyle; London, UK) was added to adjust the pH to between 7 and 7.25.

The mixture was added to a nickel tinplate DOT 2Q quality container (22.6 fl. oz. (0.668 liter)) lined with polyethylene terephthalate. The container included an exhaust valve and was activated by an actuator. The container exhausted into a tube. A first propellant sold under the brand name A-46 (26 g; Diversified CPC; Channahon, Ill.) that is a mixture of propane and isobutane (15.2% propane, 84.8% isobutane) and a second propellant that is propane and sold under the brand name A-108 (12.6 g; Diversified CPC; Channahon, Ill.) were added to the composition within the container. The two compositions were added in a ratio that generally matches the vapor pressure of an A-70 composition.

The composition produced a consistent foam that appeared homogeneous. The relative proportions of all ingredients are shown in Table 2 below.

TABLE 2

Relative proportions of ingredients used to prepare the pesticide composition of Example 2.

| Component | Inclusion (wt %) |
|---|---|
| Particulate Fipronil | 0.6593 |
| | (0.0600 active) |
| Sodium Benzoate | 0.2000 |
| Xanthan Gum | 0.1000 |
| C14 to C16 Olefin Sulfonates | 0.3000 |
| | (0.1173 active) |
| Potassium Coconut Fatty Acid | 0.2000 |
| Citric Acid | 0.0110 |
| Water | 91.0296 |
| A-46 (15.2% propane, 84.8% isobutane) | 5.0483 |
| A-108 (100% propane) | 2.4518 |

The method for producing the composition described above was used to prepare a second fipronil composition containing TERMIDOR® SC. The composition contained higher amounts of fipronil and is a suitable formulation for outdoor perimeter application. The composition is shown in Table 3 below.

TABLE 3

Relative proportions of ingredients used to prepare a second pesticide composition of Example 2.

| Component | Inclusion (wt %) |
|---|---|
| Particulate Fipronil | 7.1429 |
| | (0.6506 active) |
| Sodium Benzoate | 0.2000 |
| Xanthan Gum | 0.1500 |
| C14 to C16 Olefin Sulfonates | 0.2000 |
| | (0.0782 active) |
| Potassium Coconut Fatty Acid | 0.3000 |
| Water | 87.0071 |
| A-46 (15.2% propane, 84.8% isobutane) | 3.3655 |
| A-108 (100% propane) | 1.6345 |

Example 3

Determination of the Insecticidal Efficacy of a Pressured Foam Pesticide Composition that Includes Fipronil against Ants and Termites A pressurized pesticide composition containing fipronil (0.06 wt % active) was prepared according to the method of Example 2. A control composition containing no fipronil was also prepared and a commercial foam formulation sold under the brand name PREMISE® (Bayer Environmental Science; Research Triangle Park, N.C.) that contains imidacloprid as the pesticide active was obtained.

Each composition was applied from its container to a Petri dish three times. The Petri dish was weighed before and after application to determine the amount of material applied. The amount of pesticide composition applied to each Petri dish and the average from each composition are shown in Table 4 below.

TABLE 4

Amount of pesticide composition applied to sample Petri dishes for testing purposes.

| Treatment | Amount discharged in 1 sec (g) | Amount discharged in 5 sec (g) | Average discharge rate (g/sec) |
|---|---|---|---|
| Fipronil Foam | 1.8 | 8.8 | 1.8 |
| Composition | 1.1 | 5.5 | |
| | 2.5 | 12.6 | |
| Control (No | 2.1 | 10.6 | 2.2 |
| Fipronil) | 2.7 | 13.6 | |
| | 1.8 | 8.8 | |
| PREMISE ® Foam | 1.9 | 9.3 | 2.1 |
| | 2.0 | 10.0 | |
| | 2.5 | 12.6 | |

To test the repellency and mortality of the compositions, 15 worker carpenter ants (*Camponotus* sp.) were added to a Petri dish (150 mm diameter, 25 mm tall, 15 ants per dish) with holes drilled on opposite sides of the Petri dish. A tube was attached to each hole. One tube had been exposed to the foam composition by applying the composition into the tube for 1 second followed by drip drying overnight. The other tube was not treated. After attachment to the Petri dish, the far end of each tube was then plugged with a #1 cotton pellet soaked in 10% sucrose solution and taped shut. Fifteen (15) ants were added to the Petri dish to determine if the ants were repelled by the pesticide composition. This was repeated 4 times for each foam treatment. Dead insects were not removed. Foams tested include the fipronil foam composition of Example 2, PREMISE® Foam, the foam of Example 2 except containing no fipronil and a control in which no foam was applied. To measure repellency, the number of ants in the untreated and treated sides were counted (the ants in the center dish were not counted) and the percentage in each side relative to the total number of ants in each side (treated and untreated) was calculated. The results are shown in Table 5.

TABLE 5

Repellency and mortality results for ants introduced into a Petri dish with treated and untreated tubing attached thereto.

| Treatment | Post Exposure Time (hr) | Mean % occurrence of ants in tubes and mean % mortality | | |
|---|---|---|---|---|
| | | Treated | Untreated | Mortality |
| Fipronil Foam | 0.25 | 69.6 | 30.4 | 0.0 |
| Composition | 0.5 | 69.0 | 38.7 | 0.0 |
| | 0.75 | 61.3 | 38.7 | 0.0 |
| | 1 | 74.3 | 25.7 | 1.7 |
| | 4 | 80.0 | 20.0 | 1.7 |
| | 24 | 73.3 | 26.7 | 48.3 |
| | 48 | — | — | 96.7 |
| Blank Foam | 0.25 | 5.9 | 94.1 | 0.0 |
| Composition (the foam | 0.5 | 6.1 | 77.1 | 0.0 |
| composition of | 0.75 | 22.9 | 77.1 | 0.0 |
| Example 2 containing | 1 | 19.0 | 81.0 | 0.0 |
| no Fipronil) | 4 | 17.9 | 82.1 | 0.0 |
| | 24 | 16.9 | 83.1 | 0.0 |
| | 48 | — | — | 0.0 |
| PREMISE ® Foam | 0.25 | 7.7 | 92.3 | 0.0 |
| | 0.5 | 10.0 | 90.0 | 0.0 |
| | 0.75 | 10.0 | 90.0 | 0.0 |
| | 1 | 9.5 | 90.5 | 0.0 |
| | 4 | 9.5 | 90.5 | 0.0 |
| | 24 | 0.0 | 100.0 | 30.0 |
| | 48 | — | — | 40.0 |
| Untreated Control | 0.25 | 41.7 | 58.3 | 0.0 |
| | 0.5 | 55.3 | 45.7 | 0.0 |
| | 0.75 | 54.3 | 45.7 | 0.0 |
| | 1 | 39.5 | 60.5 | 0.0 |
| | 4 | 55.4 | 44.6 | 0.0 |
| | 24 | 44.8 | 55.2 | 0.0 |
| | 48 | — | — | 0.0 |

As may be seen from Table 5, the fipronil composition was not repellant but the blank composition was repellant. The fipronil composition resulted in significantly more mortality than the PREMISE® Foam composition.

Subterranean termites (*Reticulitermes flavipes*) were also tested to determine the repellency and mortality effect of the fipronil composition of Example 2. Three Petri dishes (100 mm diameter, 20 mm tall) were connected by tubing. The two side dishes contained colored filter paper as bait. The foam composition was applied for 1.5 seconds to one side dish and the 30 termites were added to the center dish. Dead insects were not removed from the Petri dishes. This was repeated 4 times for each foam treatment. The results are shown in Table 6 below.

TABLE 6

Repellency and mortality results for termites (Reticulitermes flavipes) introduced into the center dish of three connected Petri dishes with one dish containing various pesticide compositions.

| Treatment | Post Exposure Time (hr) | Mean % occurrence of termites in Petri dishes and mean % mortality | | |
|---|---|---|---|---|
| | | Treated | Untreated | Mortality |
| Fipronil Foam | 2 | 56.0 | 44.0 | 11.7 |
| Composition | 4 | 76.0 | 1.8 | 33.3 |
| | 24 | 98.2 | 1.8 | 59.2 |
| | 48 | — | — | 92.5 |
| Blank Foam Composition | 2 | 70.0 | 30.0 | 11.7 |
| (the foam composition of | 4 | 100.0 | 54.2 | 19.2 |
| Example 2 containing no | 24 | 45.8 | 54.2 | 20.0 |
| Fipronil) | 48 | — | — | 20.8 |

TABLE 6-continued

Repellency and mortality results for termites (Reticulitermes flavipes) introduced into the center dish of three connected Petri dishes with one dish containing various pesticide compositions.

| Treatment | Post Exposure Time (hr) | Mean % occurrence of termites in Petri dishes and mean % mortality | | |
|---|---|---|---|---|
| | | Treated | Untreated | Mortality |
| PREMISE ® Foam | 2 | 80.0 | 20.0 | 0.0 |
| | 4 | 49.2 | 50.0 | 0.0 |
| | 24 | 50.0 | 50.0 | 0.0 |
| | 48 | — | — | 0.8 |
| Untreated Control | 2 | 90.3 | 9.7 | 0.8 |
| | 4 | 95.2 | 0.0 | 0.8 |
| | 24 | 100.0 | 0.0 | 0.8 |
| | 48 | — | — | 0.8 |

As can be seen from Table 6, the fipronil composition caused higher termite mortality than the PREMISE® Foam composition.

Another repellency and mortality test was performed on drywood termites (*Incisitermes snyderi*). Comb-shaped wooden harborages were placed on opposite ends of a Petri dish (150 mm diameter, 25 mm tall). The harborages were formed by cutting 5 notches into 7.5 cm×2.5 cm×4.0 cm blocks. One harborage was treated with the respective pesticide composition inside and out and the other was untreated. Fifteen (15) termites were added to the Petri dish equidistant from the two harborages. The harborages were wetted with 1-2 drops of water to maintain their moisture level. The test was repeated four times for each composition. The results are shown in Table 7.

TABLE 7

Repellency and mortality results for termites (Incisitermes snyderi) introduced into the center dish of three connected Petri dishes with one dish containing various pesticide compositions.

| Treatment | Post Exposure Time (hr) | Mean % occurrence of termites in Petri dishes and mean % mortality | | |
|---|---|---|---|---|
| | | Treated | Untreated | Mortality |
| Fipronil Foam Composition | 0.25 | 58.3 | 41.7 | 0.0 |
| | 0.5 | 45.5 | 45.5 | 0.0 |
| | 0.75 | 54.5 | 45.5 | 0.0 |
| | 1 | 58.2 | 41.8 | 0.0 |
| | 4 | 61.8 | 38.2 | 0.0 |
| | 24 | 61.8 | 38.2 | 41.8 |
| | 48 | — | — | 96.4 |
| | 72 | — | — | 100.00 |
| Blank Foam Composition (the foam composition of Example 2 containing no Fipronil) | 0.25 | 67.3 | 32.7 | 0.0 |
| | 0.5 | 60.7 | 37.3 | 0.0 |
| | 0.75 | 62.7 | 37.3 | 0.0 |
| | 1 | 63.3 | 36.7 | 0.0 |
| | 4 | 63.3 | 36.7 | 0.0 |
| | 24 | 58.3 | 41.7 | 0.0 |
| | 48 | — | — | 10.9 |
| | 72 | — | — | 34.5 |
| PREMISE ® Foam Untreated Control | 0.25 | 70.4 | 29.6 | 0.00 |
| | 0.5 | 60.0 | 42.6 | 0.0 |
| | 0.75 | 57.4 | 42.6 | 0.0 |
| | 1 | 54.9 | 45.1 | 0.0 |
| | 4 | 52.0 | 48.0 | 0.0 |
| | 24 | 43.3 | 56.7 | 0.0 |
| | 48 | — | — | 30.9 |
| | 72 | — | — | 65.5 |
| Untreated Control | 0.25 | 32.3 | 67.7 | 0.0 |
| | 0.5 | 45.7 | 48.8 | 0.0 |
| | 0.75 | 51.2 | 48.8 | 0.0 |
| | 1 | 49.1 | 50.9 | 0.0 |
| | 4 | 54.4 | 45.6 | 0.0 |
| | 24 | 54.2 | 45.8 | 0.0 |
| | 48 | — | — | 1.8 |
| | 72 | — | — | 1.82 |

As can be seen from Table 7, the fipronil composition caused higher termite mortality than the PREMISE® Foam composition.

To further test the bioactivity of the pesticide composition of Example 2, the pesticide composition was applied directly to worker carpenter ants (*Camponotus* sp.), to subterranean termites (*Reticulitermes flavipes*) and to drywood termites (*Incisitermes snyderi*). Each respective foam composition was applied through a hole drilled through a lid of a Petri dish. In the test using ants, 15 ants were placed in a Petri dish (150 mm diameter, 25 mm tall). The fipronil foam composition and the blank foam composition were applied for 2 seconds and the PREMISE Foam composition was applied for 5 seconds. This was repeated four times for each pesticide composition. In the test involving termites, 30 termites were placed in a Petri dish (100 mm diameter, 20 mm tall) that did not contain a substrate. The fipronil foam composition and the blank foam composition were applied for 1.5 seconds and the PREMISE® Foam composition was applied for 4 seconds. The test was repeated four times for each composition. After application of the pesticide composition, the insects were removed from the treated dishes and placed into untreated Petri dishes. Dead insects were not removed from the Petri dishes. Results are shown in Table 8 below.

TABLE 8

Termite and ant mortality upon direct application of various pesticide compositions.

| Treatment | Post Exposure Time (hr) | Mean % insect mortality | |
|---|---|---|---|
| | | Carpenter ant | Subterranean termite |
| Fipronil Foam Composition | 2 | 100.0 | 98.3 |
| | 4 | 100.0 | 100.0 |
| | 24 | 100.0 | 100.0 |
| Blank Foam Composition (the foam composition of Example 2 containing no Fipronil) | 2 | 100.0 | 95.8 |
| | 4 | 100.0 | 95.8 |
| | 24 | 100.0 | 100.0 |
| PREMISE ® Foam Untreated Control | 2 | 98.3 | 100.0 |
| | 4 | 100.0 | 100.0 |
| | 24 | 100.0 | 100.0 |
| Untreated Control | 2 | 0.0 | 0.0 |
| | 4 | 0.0 | 0.0 |
| | 24 | 0.0 | 0.0 |

As can be seen from Table 8, the new fipronil composition was as effective as the commercial formulation 4 hours after application.

To further test the bioactivity of the pesticide composition of Example 2, the pesticide composition was applied indirectly to worker carpenter ants (*Camponotus* sp.), to subterranean termites (*Reticulitermes flavipes*) and to drywood termites (*Incisitermes snyderi*). The foam compositions tested were applied to Petri dishes and the foam was allowed to dissipate and dry before insects were added. In the test using ants, the fipronil foam composition and the blank foam composition were applied for 2 seconds and the PREMISE® Foam composition was applied for 5 seconds. Fifteen (15) ants were placed in a Petri dish (150 mm diameter, 25 mm tall) 24 hours after application. This was repeated four times for each pesticide composition. In the test involving *Reticulitermes flavipes*, the respective pesticide compositions were applied to Petri dishes (100 mm diameter, 20 mm tall) containing a sand substrate. After drying, the substrate was re-wetted with water. The fipronil foam composition and the blank foam composition were applied for 1.5 seconds and the PREMISE® Foam composition was applied for 4 seconds. After drying, thirty (30) termites were placed in the Petri dishes. In the test involving *Incisitermes snyderi*, the respective pesticide compositions were applied to Petri dishes (100 mm diameter, 20 mm tall) that did no contain a substrate. The fipronil foam composition and the blank foam composition were applied for 1.5 seconds and the PREMISE® Foam composition was applied for 4 seconds. Thirty (30) termites were placed in the Petri dishes. The test was repeated four times for each composition. Dead insects were not removed from the Petri dishes. Results are shown in Table 9 below.

TABLE 9

Termite and ant mortality upon indirect application of various pesticide compositions.

| Treatment | Post Exposure Time (hr) | Mean % insect mortality | | |
|---|---|---|---|---|
| | | Carpenter ant | Subterranean termite | Drywood termite |
| Fipronil Foam Composition | 1 | 0.0 | 1.7 | 3.3 |
| | 4 | 0.0 | 93.3 | 33.3 |
| | 24 | 100.0 | 100.0 | 100.0 |
| | 48 | 100.0 | 100.0 | 100.0 |
| Blank Foam Composition (the foam composition of Example 2 containing no Fipronil) | 1 | 1.7 | 2.5 | 0.0 |
| | 4 | 1.7 | 85.8 | 0.0 |
| | 24 | 39.0 | 89.2 | 1.7 |
| | 48 | 57.6 | 81.7 | 51.7 |
| PREMISE® Foam | 1 | 100.0 | 100.0 | 100.0 |
| | 4 | 100.0 | 100.0 | 100.0 |
| | 24 | 100.0 | 100.0 | 100.0 |
| | 48 | 100.0 | 100.0 | 100.0 |
| Untreated Control | 1 | 0.0 | 0.0 | 0.0 |
| | 4 | 0.0 | 0.0 | 0.0 |
| | 24 | 0.0 | 0.0 | 0.0 |
| | 48 | 0.0 | 0.0 | 0.0 |

As can be seen from Table 9, the fipronil foam composition was 100% effective at 24 hours after application.

Example 4

Comparison of a Fipronil Foam Pesticide Composition of the Present Disclosure Against Commercial Foam Formulations in Controlling Termites The fipronil pesticide composition of Example 2 was prepared. Termite populations were exposed to the fipronil pesticide composition as well as several commercially available foam compositions to determine efficacy of control. The commercial foam compositions were ALPINE® Ant and Termite Foam (BASF; Germany), FASTOUT® CS Foam (BASF; Germany) and PREMISE® Foam (Bayer Environmental Science; Research Triangle Park, N.C.). A control was also tested. ALPINE® Ant and Termite Control contains dinotefuran as the active. FASTOUT® CS Foam contains microencapsulated cyfluthrin as the active. PREMISE® Foam contains imidacloprid as the pesticide active.

The pesticide compositions were applied to Petri dishes (150 mm diameter; 25 mm tall). Two hundred (200) worker termites ($3^{rd}$ instar larva stage or older) were added to each respective Petri dish. Each trial was replicated six times for two species of termite: Eastern subterranean termites (*Reticulitermes flavipes*) and Formosan subterranean termites (*Coptotermes formosanus*). Mean mortalities were analyzed by ANOVA with means separated using Student-Newman-Keuls test at $P<0.05$. The mortality results are shown in Tables 10 and 12.

TABLE 10

Mortality of termites (*C. formasanus*) when exposed to various pesticide compositions.

| Treatment | 1 hour | 4 hours | 8 hours | 24 hours | 48 hours | 72 hours |
|---|---|---|---|---|---|---|
| Fipronil Composition | 2.16 | 2.66 | 2.83 | 128.66 | 200.00 | 200.00 |
| ALPINE® Foam | 2.16 | 3.16 | 3.83 | 15.00 | 32.66 | 70.33 |
| FASTOUT® Foam | 190.0 | 200.00 | 200.00 | 200.00 | 200.00 | 200.00 |
| PREMISE® Foam | 2.50 | 6.00 | 6.00 | 7.66 | 29.66 | 125.00 |
| Untreated Control | 0.50 | 1.33 | 2.50 | 2.83 | 3.33 | 2.00 |

TABLE 11

Mortality of termites (R. flavipes) when exposed to various pesticide compositions.

| Treatment | 1 hour | 4 hours | 8 hours | 24 hours | 48 hours | 72 hours |
|---|---|---|---|---|---|---|
| Fipronil Composition | 0.83 | 2.83 | 40.66 | 200.00 | 200.00 | 200.00 |
| ALPINE ® Foam | 0.16 | 0.16 | 1.50 | 19.50 | 147.83 | 183.66 |
| FASTOUT ® Foam | 198.00 | 200.00 | 200.00 | 200.00 | 200.00 | 200.00 |
| PREMISE ® Foam | 2.50 | 6.00 | 6.00 | 7.66 | 29.66 | 158.00 |
| Untreated Control | 0.83 | 1.00 | 1.33 | 1.83 | 1.83 | 2.16 |

As can be seen from Tables 10 and 11, the fipronil foam pesticide compositions was nearly as effective as or even more effective than commercial foam formulations.

Example 5

Efficacy of a Fipronil Foam Pesticide Composition in Controlling Worker Ants (*Camponotus modoc*)

The pressurized fipronil pesticide composition as set forth in Example 2 was prepared. Pine boards (1.9 cm in depth) were cut into sections (18.3 cm×22.5 cm). One side of each section was treated with fipronil foam by applying foam over the surface and weighing the pressurized container before and after each application. Boards were allowed to dry for 24 hours and foam was applied to the opposite side followed by drying for 24 hours. The container was weighed between applications. Water was also applied to board sections as a control and the water-treated boards were allowed to dry for 24 hours. The amount of foam and water applied to the sections is shown in Table 12 below.

TABLE 12

Amount of fipronil and pesticide applied to pine board substrates.

| Treatment | Repetition | Side 1 | Side 2 |
|---|---|---|---|
| Fipronil Composition | 1 | 10.9 | 9.8 |
| | 2 | 10.9 | 9.8 |
| | 3 | 11.1 | 9.6 |
| | 4 | 11.3 | 9.6 |
| | 5 | 11.4 | 9.8 |
| | 6 | 11.0 | 9.7 |
| Control (water) | 1 | 10.0 | 10.0 |
| | 2 | 10.0 | 10.0 |
| | 3 | 10.0 | 10.0 |
| | 4 | 10.0 | 10.0 |
| | 5 | 10.0 | 10.0 |
| | 6 | 10.0 | 10.0 |

The board sections were placed in treatment chambers (30 cm×22 cm) for 24 hours before ants were introduced. Each chamber was treated with FLOUN® to prevent ants from escaping from the chambers. Approximately a third of the chamber lids were removed to provide ventilation. A water bottle with a cotton stopper and a honey dish was added to each chamber. Ants were added 2-3 days after the pesticide compositions were applied to the board sections.

After ants were added, the ants crawled under the boards after they were introduced into the chambers. No repellency to the treated wood was observed. When boards were lifted to observe mortality, the ants remained on the treated surface. The mortality results are shown in Table 13 below.

TABLE 13

Ant mortality after exposure to fipronil foam composition and control.

| Treatment | Repetition | Number added | 1 hr | 2 hr | 4 hr | 8 hr | 18 hr | 24 hr | 30 hr | 48 hr |
|---|---|---|---|---|---|---|---|---|---|---|
| Fipronil Composition | 1 | 54 | 0 | 0 | 1 | 1 | 34 | 52 | 54 | 54 |
| | 2 | 60 | 0 | 0 | 0 | 0 | 31 | 53 | 60 | 60 |
| | 3 | 54 | 0 | 0 | 0 | 0 | 30 | 54 | 54 | 54 |
| | 4 | 58 | 0 | 0 | 0 | 0 | 24 | 44 | 58 | 58 |
| | 5 | 52 | 0 | 0 | 0 | 0 | 20 | 45 | 52 | 52 |
| | 6 | 53 | 1 | 1 | 1 | 1 | 35 | 53 | 53 | 53 |
| | Total | 331 | 1 | 1 | 2 | 2 | 174 | 301 | 331 | 331 |
| | % | — | 0.3 | 0.3 | 0.6 | 0.6 | 52.6 | 90.0 | 100.0 | 100.0 |
| Control (water) | 1 | 54 | 0 | 0 | 0 | 0 | 0 | 0 | 0 | 0 |
| | 2 | 53 | 0 | 0 | 0 | 0 | 0 | 0 | 0 | 0 |
| | 3 | 56 | 0 | 0 | 0 | 0 | 1 | 1 | 1 | 1 |
| | 4 | 55 | 0 | 0 | 0 | 0 | 0 | 0 | 0 | 0 |
| | 5 | 54 | 0 | 0 | 0 | 0 | 0 | 0 | 0 | 0 |
| | 6 | 56 | 1 | 1 | 1 | 1 | 2 | 2 | 3 | 3 |
| | Total | 328 | 1 | 1 | 1 | 1 | 3 | 3 | 4 | 4 |
| | % | — | 0.3 | 0.3 | 0.3 | 0.3 | 0.9 | 0.9 | 1.2 | 1.2 |

As can be seen from Table 13, no mortality was observed at 1, 2, 4 or 8 hours. At 18 hours, over a 50% mortality was observed which increased to 90% in 24 hours.

Example 6

Comparison of a Fipronil Foam Pesticide Composition of the Present Disclosure against Commercial Foam Formulations in Controlling Ants Artificial carpenter ant nests were constructed from pine wood (2 in×8 in (5.1 cm×20.3 cm)). Sections of wood (10 in long (25.4 cm)) with parallel, 1.5 in (3.8 cm) diameter holes drilled lengthwise into the board, but ending just before breaking through the back end were used as nests. To connect these two parallel galleries, a third hole was drilled from one side of the board to the other, perpendicular to and across the path of the parallel galleries, thereby connecting all three galleries together. The board was then cut lengthwise down the center, resulting in two galleried pieces of wood that mirrored one another.

Ants were exposed to the fipronil pesticide composition prepared according to Example 2 as well as several commercially available foam compositions to determine efficacy of control. The commercial foam compositions were PREMISE® Foam (Bayer Environmental Science; Research Triangle Park, N.C.) and CYKICK® aerosol (BASF; Germany) which contains cyfluthrin as an active. For both foams, one-half of each pair of blocks (n=5 blocks per treatment) was treated with enough foam to completely coat the inside of all galleries (i.e., foam was injected into one hole until it ran from all other holes in the wood block). For CYKICK®, a one to two-second burst was squirted into each gallery. For each of the three pesticide treatments, the sister-side was left untreated. For the untreated control treatment, neither side was treated. The next day, after the insecticide treatments had dried, masking tape was applied to all exposed surfaces of each block in order to cover those areas where treatment was inadvertently applied. Applying insecticides into a block's galleries sometimes resulted in insecticide residue on the outside surface of blocks. In order to be sure that resultant ant mortality was from insecticide residues inside the blocks, all exposed, external surfaces of wood were covered with masking tape so that ants were not inadvertently killed as they crawled on the outside surface of the wood blocks. After blocks were wrapped in tape, the treated-untreated block pairs were put back together on the floor of a FLOUN®-lined, plastic box (31 cm deep×23 cm wide×10 cm high). Twenty (20) carpenter ants were added to each box. The following day, the number of ants alive and dead/dying inside each block (and outside either block but inside the plastic box) was recorded. Dying ants were defined as those that were twitching, unable to crawl and/or right themselves and/or exhibited an agitated gait with legs in a spread eagle fashion with open jaws. When probed or touched, many of these dying ants would bring their head up, exposing its mandibles in an open and aggressive manner. Each of the four treatments was replicated 5 times.

Ninety-eight to 100 of the 100 ants used in each treatment (20 ants per replicate×5 replicates per treatment) were recovered. One or two ants in just four of the 20 replicates escaped during the counting process and could not be accounted for. In the remaining 16 replicates, all 20 ants were accounted for. This did not appreciably affect our results. No ants died (0% mortality) in either the Untreated Control or Premise Foam treatments, while just 3% were killed by the CYKICK® treatment. Conversely, all ants (100%) were dead/dying one day after being introduced into fipronil foam-treated wood blocks; by the second day, all were completely dead Notably, 93% of the dead/dying ants on day one post-treatment in the fipronil foam treatment were discovered on the floor of the plastic box (i.e., not inside either block).

In the three treatments exhibiting zero to little mortality (CYKICK®, PREMISE® foam and Control) just 6-7% of ants were discovered in the open, and not inside either wood block, at the time data were tallied. The remaining ants were found harboring inside the wood blocks. In the untreated control, for instance, 74% (68 of 92 ants) of the ants that were found inside a wood block were found inside the block on the left side, while the remaining 26% of ants found inside a wood block (24 of 92 live ants) were found harboring inside the block on the right side. In the CYKICK® treatment, 100% (93 of 93 ants) of the ants that were found inside a wood block were found inside the untreated block. In the PREMISE® foam treatment, 77% (72 of 94 ants) of the ants that were found inside a wood block were found inside the block on the left side (untreated block), while the remaining 23% of the ants that were found inside a wood block (22 of 94 live ants) were found harboring inside the PREMISE foam-treated block. Notably, none of the ants found harboring inside the PREMISE®-foam treated block were dead or seemed to be adversely affected. The results of the testing are shown in Table 14 below ("L"=live, "D"=dead).

TABLE 14

Repellency and mortality for ant populations exposed to various pesticide compositions.

| Treatment | Rep | Ants Inside Untreated Block (Left Side) | | Ants Inside Untreated Block (Right Side) | | Ants In Plastic Box But Outside Wood Blocks | | Total | Colony | Block | Mortality % |
|---|---|---|---|---|---|---|---|---|---|---|---|
| | | L | D | L | D | L | D | | | | |
| Fipronil Foam | 1 | 0 | 1 | 0 | 0 | 0 | 18 | 19 | 16 | 2 | 100 |
| | 2 | 0 | 2 | 0 | 2 | 0 | 16 | 20 | 29 | 14 | 100 |
| | 3 | 0 | 0 | 0 | 2 | 0 | 18 | 20 | 16 | 17 | 100 |
| | 4 | 0 | 0 | 0 | 0 | 0 | 20 | 20 | 39 | 10 | 100 |
| | 5 | 0 | 0 | 0 | 0 | 0 | 19 | 19 | 16 | 22 | 100 |

TABLE 14-continued

Repellency and mortality for ant populations exposed to various pesticide compositions.

| Treatment | Rep | Ants Inside Untreated Block (Left Side) | | Ants Inside Untreated Block (Right Side) | | Ants In Plastic Box But Outside Wood Blocks | | Total | Colony | Block | Mortality % |
|---|---|---|---|---|---|---|---|---|---|---|---|
| | | L | D | L | D | L | D | | | | |
| PREMISE ® Foam | 1 | 7 | 0 | 8 | 0 | 5 | 0 | 20 | 16 | 16 | 0 |
| | 2 | 13 | 0 | 7 | 0 | 0 | 0 | 20 | 39 | 5 | 0 |
| | 3 | 13 | 0 | 6 | 0 | 1 | 0 | 20 | 16 | 7 | 0 |
| | 4 | 20 | 0 | 0 | 0 | 0 | 0 | 20 | 39 | 12 | 0 |
| | 5 | 19 | 0 | 1 | 0 | 0 | 0 | 20 | 39 | 21 | 0 |
| CYKICK ® | 1 | 18 | 0 | 0 | 0 | 0 | 2 | 20 | 16 | 23 | 10 |
| | 2 | 20 | 0 | 0 | 0 | 0 | 0 | 20 | 39 | 3 | 0 |
| | 3 | 17 | 0 | 0 | 0 | 2 | 1 | 20 | 16 | 9 | 5 |
| | 4 | 19 | 0 | 0 | 0 | 1 | 0 | 20 | 39 | 19 | 0 |
| | 5 | 19 | 0 | 0 | 0 | 0 | 0 | 19 | 16 | 13 | 0 |
| Untreated Control | 1 | 14 | 0 | 2 | 0 | 4 | 0 | 20 | 16 | 20 | 0 |
| | 2 | 9 | 0 | 11 | 0 | 0 | 0 | 20 | 39 | 8 | 0 |
| | 3 | 15 | 0 | 2 | 0 | 2 | 0 | 19 | 16 | 11 | 0 |
| | 4 | 13 | 0 | 6 | 0 | 1 | 0 | 20 | 39 | 1 | 0 |
| | 5 | 17 | 0 | 3 | 0 | 0 | 0 | 20 | 39 | 15 | 0 |

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatus and methods without departing from the scope of the invention, it is intended that all matter contained in the above description and shown in the accompanying figures shall be interpreted as illustrative and not in a limiting sense.

What is claimed is:

1. A ready-to-use foamable pesticide composition comprising:
   a diluent;
   particulate fipronil suspended in the diluent;
   a thickening agent; and
   a surfactant system comprising potassium coconut fatty acid and an alpha olefin sulfonate.

2. A ready-to-use foamable pesticide composition as set forth in claim 1 wherein the thickening agent is selected from the group consisting of bentonite clay, xanthan gum, guar gum, gum arabic, alginin, gum tragacanth and sodium alginate.

3. A ready-to-use foamable pesticide composition as set forth in claim 1 wherein the thickening agent is xanthan gum.

4. A ready-to-use foamable pesticide composition as set forth in claim 1 comprising a foam stabilizer.

5. A ready-to-use foamable pesticide composition as set forth in claim 4 wherein the thickening agent is also the foam stabilizer.

6. A ready-to-use foamable pesticide composition as set forth in claim 1 wherein the composition is capable of remaining in a foam phase for less than about 2 minutes after application.

7. A ready-to-use foamable pesticide composition as set forth in claim 1 wherein the diluent is water.

8. A ready-to-use foamable pesticide composition as set forth in claim 1 wherein the composition comprises at least about 0.005% by weight particulate fipronil.

9. A ready-to-use foamable pesticide composition as set forth in claim 1 wherein the average nominal diameter of the particulate fipronil is less than about 50 μm.

10. A ready-to-use foamable pesticide composition as set forth in claim 1 wherein the composition comprises a propellant and the total amount of propellants in the pesticide composition is at least about 1% by weight of the composition.

11. A ready-to-use foamable pesticide composition as set forth in claim 1 wherein the composition is not an emulsion.

* * * * *